US010039745B2

(12) United States Patent
Mosher et al.

(10) Patent No.: US 10,039,745 B2
(45) Date of Patent: *Aug. 7, 2018

(54) ENALAPRIL FORMULATIONS

(71) Applicant: Silvergate Pharmaceuticals, Inc., Greenwood Village, CO (US)

(72) Inventors: Gerold L. Mosher, Kansas City, MO (US); David W. Miles, Kansas City, MO (US)

(73) Assignee: SILVERGATE PHARMACEUTICALS, INC., Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/802,341

(22) Filed: Nov. 2, 2017

(65) Prior Publication Data

US 2018/0055821 A1  Mar. 1, 2018

Related U.S. Application Data

(63) Continuation of application No. 15/613,622, filed on Jun. 5, 2017, now Pat. No. 9,808,442, which is a continuation of application No. 15/081,603, filed on Mar. 25, 2016, now Pat. No. 9,669,008.

(60) Provisional application No. 62/310,198, filed on Mar. 18, 2016.

(51) Int. Cl.
*A61K 31/401* (2006.01)
*A61K 9/00* (2006.01)
*A61K 47/26* (2006.01)
*A61K 47/12* (2006.01)

(52) U.S. Cl.
CPC .......... *A61K 31/401* (2013.01); *A61K 9/0053* (2013.01); *A61K 9/0095* (2013.01); *A61K 47/12* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 4,374,829 A | 2/1983 | Harris et al. | |
| 4,472,380 A | 9/1984 | Harris et al. | |
| 4,510,083 A | 4/1985 | Blacklock et al. | |
| 4,743,450 A | 5/1988 | Harris et al. | |
| 4,793,998 A | 12/1988 | Murthy et al. | |
| 4,830,853 A | 5/1989 | Murthy et al. | |
| 4,931,430 A | 6/1990 | Sudilovsky et al. | |
| 5,049,553 A | 9/1991 | Sudilovsky | |
| 5,698,562 A | 12/1997 | Mendes et al. | |
| 6,028,222 A | 2/2000 | Dietlin et al. | |
| 6,300,361 B1 | 10/2001 | Vivilecchia et al. | |
| 6,300,362 B1 | 10/2001 | Vivilecchia et al. | |
| 6,413,988 B1 | 7/2002 | De | |
| 6,509,350 B2 | 1/2003 | Vivilecchia et al. | |
| 6,790,861 B2 | 9/2004 | Vivilecchia et al. | |
| 6,869,963 B2 | 3/2005 | Patel et al. | |
| 6,977,257 B2 | 12/2005 | Parab et al. | |
| 7,101,888 B2 | 9/2006 | Reo et al. | |
| 7,605,148 B2 | 10/2009 | Batta et al. | |
| 8,153,824 B2 | 4/2012 | Sesha | |
| 8,568,747 B1 | 10/2013 | Rajewski et al. | |
| 8,778,366 B2 | 7/2014 | Rajewski et al. | |
| 8,927,028 B2 | 1/2015 | Grenier et al. | |
| 9,463,183 B1 | 10/2016 | Mosher et al. | |
| 9,616,096 B1 | 4/2017 | Mosher et al. | |
| 9,669,008 B1 | 6/2017 | Mosher et al. | |
| 9,855,214 B2 | 1/2018 | Rajewski et al. | |
| 2004/0171669 A1 | 9/2004 | Chenevier | |
| 2004/0258757 A1 | 12/2004 | Bosch et al. | |
| 2006/0094760 A1 | 5/2006 | Fawzy et al. | |
| 2006/0121066 A1 | 6/2006 | Jaeger et al. | |
| 2007/0265344 A1 | 11/2007 | Strobel et al. | |
| 2008/0221156 A1 | 9/2008 | Spireas | |
| 2008/0234291 A1 | 9/2008 | Francois et al. | |
| 2009/0269287 A1 | 10/2009 | Berta | |
| 2010/0222334 A1 | 9/2010 | Talamonti et al. | |
| 2011/0003798 A1 | 1/2011 | Okram et al. | |
| 2014/0100260 A1 | 4/2014 | Rajewski et al. | |
| 2015/0148335 A1 | 5/2015 | Bova et al. | |
| 2015/0258027 A1 | 9/2015 | Rajewski et al. | |
| 2017/0119840 A1 | 5/2017 | Mosher et al. | |
| 2017/0181968 A1 | 6/2017 | Rajewski et al. | |
| 2017/0266159 A1 | 9/2017 | Mosher et al. | |

FOREIGN PATENT DOCUMENTS

| | | |
|---|---|---|
| CA | 1275350 C | 10/1990 |
| EP | 2903690 A1 | 8/2015 |
| WO | WO-9814196 A1 | 4/1998 |
| WO | WO-9930690 A1 | 6/1999 |

(Continued)

OTHER PUBLICATIONS

AAPS American Association of Pharmaceutical Scientists, Preliminary Program, 2011 AAPS Annual Meeting and Exposition, Washington, D.C., Oct. 23-27, 2011, 112 pages.

Ahlin et al., "Investigation of polymeric nanoparticles as carriers of enalaprilat for oral administration," Int'l. Journ. Pharmaceutics, 239, pp. 113-120 (2002).

Allen et al., "Stability of alprazolam, chloroquine phosphate, cisapride, enalapril maleate, and hydralazine hydrochloride in extemporaneously compounded oral liquids," Am J. Health-Syst Pharm, vol. 55, pp. 1915-1920, (1998).

Allen, Lisinopril 1 mg/mL oral liquid US Pharm., 38(2):36-37 (2013).

Al-Omari et al. "Effect of the drug-matrix on the stability of enalapril maleate in tablet formulations" Journal of Pharmaceutical and Biomedical Analysis, 2001, vol. 25:893-902.

(Continued)

*Primary Examiner* — Jeffrey S Lundgren
*Assistant Examiner* — Stephanie K Springer
(74) *Attorney, Agent, or Firm* — Wilson, Sonsini, Goodrich & Rosati

(57) ABSTRACT

Provided herein are stable enalapril oral liquid formulations. Also provided herein are methods of using enalapril oral liquid formulations for the treatment of certain diseases including hypertension, heart failure and asymptomatic left ventricular dysfunction.

20 Claims, 2 Drawing Sheets

(56) References Cited

FOREIGN PATENT DOCUMENTS

| WO | WO-0145667 A2 | 6/2001 |
|---|---|---|
| WO | WO-02089775 A1 | 11/2002 |
| WO | WO-2007070843 A2 | 6/2007 |
| WO | WO-2009116078 A2 | 9/2009 |
| WO | WO-2011031462 A2 | 3/2011 |
| WO | WO-2011128783 A2 | 10/2011 |
| WO | WO-2012085249 A2 | 6/2012 |
| WO | WO-2014055667 A1 | 4/2014 |
| WO | WO-2014178065 A1 | 11/2014 |
| WO | WO-2017075368 A1 | 5/2017 |
| WO | WO-2017161339 A1 | 9/2017 |

OTHER PUBLICATIONS

Bhardwaj et al., "Study of forced degradation behavior of enalapril maleate by LC and LC-MS and development of a validated stability-indicating assay method," Journ. Pharmac. and Biomed. Analysis, 46, pp. 113-120 (2008).

Blowey, "Update on the pharmacologic treatment of hypertension in pediatrics," Journal of Clinical Hypertension (Hoboken, NJ, United States) (2012), 14(6), 383-387. Database: CAPLUS, DOI:10.1111/j.1751-7176.2012.00659.x.

Boukarim et al., Preservatives in liquid pharmaceutical preparations. The Journal of Applied Research, 9(1 & 2):14-17, 2009.

Bourgault et al., "Reference-based pricing of prescription drugs: exploring the equivalence of angiotensin-converting-enzyme inhibitors," CMAJ, 161:255-60 (1999).

Brilla et al., Lisinopril-Mediated regression of myocardial fibrosis in patients with hypertensive heart disease. Circulation, 102:1388-1393, 2000.

Cabot Corporation, "Influence of CAB-O-SIL® M-5P on the Angle of Repose and Flow Rates of Pharmaceutical Powders," 10 pages (2004).

Calabro et al., "Hemodynamic effects of a single oral dose of enalapril among children with asymptomatic chronic mitral regurgitation," American Heart Journal (1999), 138(5, Pt. 1), 955-961.

Definition of Hypertension (1 page) retrieved from: http://medical-dictionary.thefreedictionary.com/hypertension. No date available, 2018.

Delucchi et al., "Enalapril and prednisone in children with nephrotic-range proteinuria," Pediatric nephrology (Berlin, Germany) (2000), 14(12), 1088-91, Database: MEDLINE.

Drug Information on Enalapril (3 pages), 2001. retrieved from: http://www.accessdata.fda.gov/drugsatfda_docs/nda/2001/18-998s058_Vasotec.cfm.

drugs.com. Enalapril Tablets Soluble. Website [online]. [available online May 9, 2010] [retrieved on Jan. 16, 2014], 11 pages. Retrieved from the Internet< URL: https://web.archive.org/web/20100509220009/http://www.drugs.com/pro/enalapril-tablets-soluble.html>.

European Patent Application No. 13844343.7 Extended European Search Report dated Feb. 19, 2016.

Garrett, Edward R. Prediction of stability of drugs and pharmaceutical preparations. Journal of Pharmaceutical Sciences, 51(9):811-833, 1962.

Glass and Haywood, Stability considerations in liquid dosage forms extemporaneously prepared from commercially available products. J Pharmaceut Science, 9(3):398-426, 2006.

Gulf Cooperation Council. The GCC Guidelines for Stability Testing of Drug Substances and Pharmaceutical Products. Publication [online]. Edition Two, 1428 H-2007 G [available online Jul. 2011] [retrieved on Feb. 3, 2014]. Retrieved from the Internet:< URL: https://web.archive.org/web/20110726040053/http://www.ich.org/fileadmin/Public_Web_Site/ABOUT_ICH/Organisation/GCC/Topics under_Harmonisation/Stability.pdf>. p. 22, 2.9 .3; p. 25, 2.9.7.

Handbook of Pharmaceutical Excipients, Fifth edition, edited by Raymond C. Rowe et al., London: Pharmaceutical Press, 2006, (monographs for citric acid monohydrate, sodium benzoate, sodium citrate, sodium hydroxide, and xylitol), 23 pages.

Harris, Daniel C. Exploring Chemical Analysis, 4th edition. New York:W.H. Freeman and Company, 2009 (Chapters 8,9,21 and 22), 105 pages.

Hensel et al., Transesterification reactions off parabens (Alkyl 4-Hydroxybenzoates) with polyols in aqueous solution Journal of Pharmaceutical Sciences, 84(1):115-119, 1995.

Hsu et al., Enalapril in Infants With Single Ventricle: Results of a Multicenter Randomized Trial; DOI:10.1161/CirculationAHA.109.927988Richard V.; et al From Circulation (2010), 122(4), 333-340. Database: CAPLUS,.

Hsu et al., "Rationale and design of a trial of angiotensin-converting enzyme inhibition in infants with single ventricle," American Heart Journal (2009), 157(1), 37-45. Database: CAPLUS, DOI:10.1016/j.ahj.2008.08.030.

Kalaitzidis et al. Prehypertension: is it relevant for nephrologists? Kidney International, 2010, 77:194-200.

Li et al., "Lessons learned from a pediatric clinical trial: The Pediatric Heart Network Angiotensin-Converting Enzyme Inhibition in Mitral Regurgitation Study," American Heart Journal (2011), 161(2), 233-240. Database: CAPLUS, DOI:10.1016/j.ahj.2010.10.030.

Lima et al., "Stability and in vitro release profile of enalapril maleate from different commercially available tablets: Possible therapeutic implications," Journ. Pharmac. And Biomed. Analysis, 47, pp. 934-937 (2008).

Lipshultz, "Exposure to anthracyclines during childhood causes cardiac injury," Seminars in Oncology (2006), 33(3, Suppl. 8), S8-S14., Database: CAPLUS, DOI:10.1053/j.seminoncol.2006.04.019.

Ma et al., HPLC and LC-MS studies of the transesterification reaction of Methylparaben with twelve 3- to 6-carbon sugar alcohols and propylene glycol and the isomerization of the reaction products by acyl migration. Journal of Chromatograaphic Science, 40(3):170-177, 2002.

Meyers et al. Pharmacotherapy Review of Chronic Pediatric Hypertension. Clinical Therapeutics (2011), 33(10), 1331-1356. Database: CAPLUS, DOI:10.1016/j.clinthera.2011.09.003.

Miller et al., "Enalapril: a well-tolerated and efficacious agent for the paediatric hypertensive patient," Journal of hypertension. Supplement : official journal of the International Society of Hypertension (1986), 4(5), S413-6, Database: MEDLINE.

Miller et al., "Enalapril: a well-tolerated and efficacious agent for the pediatric hypertensive patient," Journal of cardiovascular pharmacology (1987), 10 Suppl 7S154-6, Database: MEDLINE.

Mir et al., "Effect of carvedilol on QT duration in pediatric patients with congestive heart failure," Clinical Drug Investigation (2004), 24(1), 9-15. Database: CAPLUS, DOI:10.2165/00044011-200424010-00002.

Momma, "ACE inhibitors in pediatric patients with heart failure," Paediatric drugs (2006), 8(1), 55-69, Database: MEDLINE.

Nahata et al.Stability of enalapril maleate in three extemporaneously prepared oral liquids. Am. J. Health-Syst Pharm 55:1155-1157 (1998).

Nakamura et al., "The kinetic profiles of enalapril and enalaprilat and their possible developmental changes in pediatric patients with congestive heart failure," Clinical pharmacology and therapeutics (1994), 56(2), 160-8, Database: MEDLINE.

National institutes of Health. 'MedlinePius: Hypertension'. Website [online]. [available online May 20, 2012] [retrieved on Jan. 16, 2014], 5 pages. Retrieved from the Internet< URL:https://web.archive.org/web/20120520035026/http://www.nlm.nih.gov/medlineplus/ency/article/000468.htm>.

Nationwide Children's Hospital. 'Enalapril Oral Suspension' Publication [online]. Mar. 29, 2010 [retrieved on Jan. 14, 2014], 1 page. Retrieved from the Internet< URL:http://www.nationwidechildrens.org/Document/Get/78785>.

Niazi, Sarfaraz K. Handbook of Pharmaceutical Manufacturing Formulations: Liquid Products, vol. 3, Second edition. New York: Informa Healthcare USA, Inc., 2009, 400 pages.

(56) References Cited

OTHER PUBLICATIONS

Nicolosi et al., The prognostic value of predischarge quantitative two-dimensional echocardiographic measurements and the effects of early lisinopril treatment on left ventricular structure and function after acute myocardial infarction in the GISSI-3 trial. European Heart Journal, 17:1646-1656, 1996.
*Novartis AG* (Appellants) v. *Torrent Pharmaceuticals Limited, Apotex Inc., Mylan Pharmacuticals Inc.*, (Appellees), No. 2016-1352, Slip Opinion decided Apr. 12, 2017, 27 pages.
Nunn et al. Formulation of medicines for children. British Journal of Clinical Pharmacology, 59:6, pp. 674-676 (2005).
Packer et al., Comparative effects of low and high doses of the angiotensin-converting enzyme inhibitor, lisinopril, on morbidity and mortality in chronic heart failure. Circulation, 100:2312-1218, 1999.
Patel et al., "Extemporaneous Dosage Form for Oral Liquids," Pharmacophore, vol. 2, No. 2, pp. 86-103 (2011).
PCT/US2016/059348 International Search Report and Written Opinion dated Jan. 3, 2017.
PCT/US2013/63096 International Preliminary Report on Patentability dated Apr. 7, 2015.
PCT/US2013/63096 International Search Report and Written Opinion dated Feb. 20, 2014.
PCT/US2017/023074 International Search Report and Written Opinion dated Jun. 16, 2017.
Product Information of Bicitra, "Sodium Citrate and Citric Acid Oral Solution USP." 2 pages.
Product Information of Ora-Sweet (1 page, 2013) retrieved from, http://www.stobec.com/documents/data/8196.pdf.
Proesmans et al., "Enalapril in children with Alport syndrome," Pediatric nephrology (Berlin, Germany) (2004), 19(3), 271-5, Database: MEDLINE.
Proesmans et al., Long-term therapy with enalapril in patients with nephrotic-range proteinuriam, Pediatric nephrology (Berlin, Germany) (1996), 10(5), 587-9, Database: MEDLINE.
Prosemans et al., "Enalapril in pediatric patients with Alport syndrome: 2 years' experience," European Journal of Pediatrics (2000), 159(6), 430-433. Database: CAPLUS, DOI:10.1007/s004310051301.
Raia, et al., Angiotensin-converting enzyme inhibitors: A Comparative review. DPIC, The Annuals of Pharmacotherapy, 24:506-525, 1990.
Ramusovic et al., "Determination of enalapril and enalaprilat in small human serum quantities for pediatric trials by HPLC-tandem mass spectrometry," Biomedical Chromatography (2012), 26(6), 697-702.
Rezende et al., "Stability and Compatibility Study on Enalapril Maleate Using Thermoanalytical Techniques," Journ Thermal Analysis and Calorimetry, 93:3, pp. 881-886 (2008).
Rippley et al., "Pharmacokinetic Assessment of an Oral Enalapril Suspension for Use in Children," Biopharmaceutics & Drug Disposition 21:339-344 (2000).
Rose et al., Stability of Lisinopril syrup (2 mg/mL) extemporaneously compounded from tablets. Int J Pharm Compd. 4(5):398-399 (2000).
Russell, Craig Allen, Paediatric Drug Development:—Reformulation, In Vitro, Genomic and In Vivo Evaluation. Thesis, Apr. 2014, 330 pages.
Sandoz, Limited. Amoxicillin 125 mg/5 ml Powder for Oral Suspension. Product brochure [online]. Jul. 2012 [retrieved on Jan. 17, 2014]. Retrieved from the Internet< URL:http://www.drugs.com/uklpdf/leaflet/196044.pdf>.
Schlatter et al., Stability of Enalapril solutions prepared from tablets in sterile water. Australian J. Hospital Pharmacy, 27:395, 1997.
Seikaly. Hypertension in children: an update on treatment strategies. Current Opinion in Pediatrics, 19:170-177, 2007.
Silber et al., "Design and baseline characteristics for the ACE inhibitor after anthracycline (AAA) study of cardiac dysfunction in long-term pediatric cancer survivors," American Heart Journal (2001), 142(4), 577-585. Database: CAPLUS, DOI:10.1067/mhj.2001.118115.
Silber et al., "Enalapril to prevent cardiac function decline in long-term survivors of pediatric cancer exposed to anthracyclines," Journal of Clinical Oncology (2004), 22(5), 820-828. Database: CAPLUS, DOI:10.1200/JCO.2004.06.022.
Simončič et al., "Use of microcalorimetry in determination of stability of enalapril maleate and enalapril maleate table formulations," Int'l. Journ. Pharmaceutics, 342, pp. 145-151 (2007).
Sipahi et al. Effect of Antihypertensive Therapy on Incident Stroke in Cohorts with Prehypertensive Blood Pressure Levels: A Meta-Analysis of Randomized Controlled Trials, Stroke: Journal of the America! Heart Association (online], Dec. 8, 2011 (retrieved Jan. 16, 2014]. 10 pages. Retrieved from the Internet< URL:http://www.medpagetoday.com/upload/2011/12/9/Stroke-2011-Sipahi-STROKEAHA.111.636829.pdf>.
Sipahi et al., Effects of normal, pre-hypertensive, and hypertensive blood pressure levels on progression of coronary atherosclerosis, J. Am. Coll. Cardiol. 48, 833-838, 2006.
Sosnowska et al., "Stability of Extemporaneous Enalapril Maleate Suspensions for Pediatric Use Prepared from Commercially Available Tablets," Acta Poloniae Pharmaceutica, vol. 66, No. 3, pp. 321-326 (2009).
Standing et al. Paediatric formulations—Getting to the heart of the problem. International Journal of Pharmaceutics (2005), 300(1-2), 56-66. Database: CAPLUS.
Stanisz, "Evaluation of stability of enalapril maleate in solid phase," Journ. Pharma. and Biomed. Analysis, 31, pp. 375-380 (2003).
TEVA UK, Limited. Enalapril Maleate 2.5 mg, 5 mg, 10 mg and 20 mg Tablets. Product Brochure [online]. Mar. 2011 [retrieved on Jan. 14, 2014], 8 pages. Retrieved from the Internet< URL:http://www.drugs.com/uk/pdf/leaflet/213793.pdf>. column 2, lines 70-76.
Thompson et al., Characterization of an entemporaneous liquid formulation of lisinopril. Am J Health Syst Pharm. 60(1):69-74 (2003).
Tian et al., Effect of organic anion-transporting polypeptide 1B1 (OATP1B1) polymorphism on the single- and multiple-dose pharmacokinetics of enalapril in healthy Chinese adult men Clinical Therapeutics, 33(5): 655 (2011).
U.S. Appl. No. 13/670,355 Office Action dated Feb. 8, 2013.
U.S. Appl. No. 13/670,355 Office Action dated Jul. 30, 2013.
U.S. Appl. No. 13/914,452 Office Action dated Aug. 28, 2013.
U.S. Appl. No. 14/433,502 Office Action dated Dec. 29, 2016.
U.S. Appl. No. 14/433,502 Restriction Requirement dated Apr. 12, 2016.
U.S. Appl. No. 14/934,752 First Action Interview dated Jan. 25, 2016.
U.S. Appl. No. 14/934,752 Office Action dated Apr. 26, 2016.
U.S. Appl. No. 15/081,603 First Action Interview dated Sep. 2, 2016.
U.S. Appl. No. 15/081,603 First Action Interview Office Action Summary dated Jan. 17, 2017.
U.S. Appl. No. 15/268,095 Office Action dated Oct. 13, 2016.
U.S. Appl. No. 15/433,743 Office Action dated Jun. 5, 2017.
U.S. Appl. No. 15/613,622 Office Action dated Aug. 11, 2017.
Van Hecken et al. Absence of a pharmacokinetic interaction between enalapril and frusemide British Journal of Clinical Pharmacology, 1987, vol. 23:84-87.
VASOTEC (Enalapril Maleate) Product Insert (2010) 5 pages (Best copy available).
Wang et al., "Eudragit E Accelerated the Diketopiperazine Formation of Enalapril Maleate Determined by Thermal FTIR Microspectroscopic Technique," Pharmaceutical Research, vol. 21, No. 11, Nov. 2004.
Webster et al., The Stability of Lisinopril as an extemporaneous syrup. Int J Pharm Compd. 1(5):352-353 (1997).
Wells et al., "A double-blind, placebo-controlled, dose-response study of the effectiveness and safety of enalapril for children with hypertension," Journal of Clinical Pharmacology (2002), 42(8), 870-880.

(56) References Cited

OTHER PUBLICATIONS

Wells et al., "The Pharmacokinetics of Enalapril in Children and Infants with Hypertension," J. Clin Pharmacol 41:1064-1074 (2001).
Williams et al, "Factors affecting growth in infants with single ventricle physiology: a report from the Pediatric Heart Network Infant Single Ventricle Trial," The Journal of Pediatrics (2011), 159(6).
Liern et al., "The additive antiproteinuric effect of Enalapril and Losartan to normotensive patients with pathology proteinuria," Nefrologia : publicacion oficial de la Sociedad Espanola Nefrologia (2004), 24(6), 553-8, Database: MEDLINE (with English abstract).
Rokicki, "Use of converting enzyme inhibitors in children. I. General remarks," Wiadomosci lekarskie (Warsaw, Poland : 1960) (1997), 50(1-3), 28-31, Database: MEDLINE (with English abstract).
U.S. Appl. No. 15/850,732 Office Action dated Mar. 1, 2018.

ENALAPRIL FORMULATIONS

CROSS-REFERENCE OF RELATED APPLICATIONS

This application is a continuation of U.S. patent application Ser. No. 15/613,622, filed Jun. 5, 2017, which is a continuation of U.S. patent application No. 15/081,603, filed Mar. 25, 2016 (now U.S. Pat. No. 9,669,008, issued Jun. 06, 2017), which claims the benefit of U.S. Provisional Patent Application No. 62/310,198, filed Mar. 18, 2016, all of which are incorporated herein by reference in their entirety.

BACKGROUND OF THE INVENTION

Hypertension, or high blood pressure, is a serious health issue in many countries. According to the National Heart Blood and Lung Institute, it is thought that about 1 in 3 adults in the United States alone have hypertension. Left unchecked, hypertension is considered a substantial risk factor for cardiovascular and other diseases including coronary heart disease, myocardial infarction, congestive heart failure, stroke and kidney failure. Hypertension is classified as primary (essential) hypertension or secondary hypertension. Primary hypertension has no known cause and may be related to a number of environmental, lifestyle and genetic factors such as stress, obesity, smoking, inactivity and sodium intake. Secondary hypertension can be caused by drug or surgical interventions, or by abnormalities in the renal, cardiovascular or endocrine system.

A number of antihypertensive drugs are available for treating hypertension. Various therapeutic classes of antihypertensive drugs include alpha-adrenergic blockers, beta-adrenergic blockers, calcium-channel blockers, hypotensives, mineralcorticoid antagonists, central alpha-agonists, diuretics and rennin-angiotensin-aldosterone inhibitors which include angiotensin II receptor antagonists (ARB) and angiotensin-converting enzyme (ACE) inhibitors. Angiotensin-converting enzyme (ACE) inhibitors inhibit angiotensin-converting enzyme (ACE), a peptydyl dipeptidase that catalyzes angiotension I to angiotension II, a potent vasoconstrictor involved in regulating blood pressure.

Enalapril is a prodrug belonging to the angiotensin-converting enzyme (ACE) inhibitor of medications. It is rapidly hydrolyzed in the liver to enalaprilat following oral administration. Enalaprilat acts as a potent inhibitor of ACE. The structural formulae of enalapril and enalaprilat are as follows:

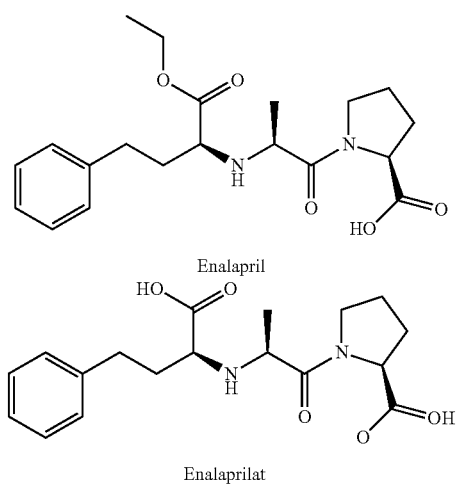

Enalapril

Enalaprilat

Enalapril is currently administered in the form of oral tablets, (e.g., Vasotec®) or in the form of liquid formulations obtained by reconstitution of enalapril powder formulations. In addition to the treatment of hypertension, enalapril tablets have been used for symptomatic congestive heart failure, and asymptomatic left ventricular dysfunction.

SUMMARY OF THE INVENTION

Provided herein are enalapril oral liquid formulations. In one aspect, the enalapril oral liquid formulation, comprises (i) enalapril or a pharmaceutically acceptable salt or solvate thereof; (ii) a sweetener that is sucralose (iii) a buffer comprising citric acid; (iv) a preservative that is sodium benzoate; and (v) water; wherein the pH of the formulation is less than about 3.5; and wherein the formulation is stable at about 5±3° C. for at least 12 months.

In some embodiments, the enalapril is enalapril maleate. In some embodiments, the formulation further comprises a flavoring agent. In some embodiments, the buffer in the formulation further comprises sodium citrate dihydrate. In some embodiments, the amount of enalapril or a pharmaceutically acceptable salt or solvate thereof is about 0.6 to about 1.2 mg/ml. In some embodiments, the amount of sucralose is about 0.5 to about 0.9 mg/ml. In some embodiments, the amount of citric acid in the buffer is about 0.8 to about 3.5 mg/ml. In some embodiments, the amount of sodium citrate dihydrate in the buffer is about 0.1 to about 0.80 mg/ml. In some embodiments, the amount of the sodium benzoate is about 0.2 to about 1,2 mg/ml. In some embodiments, the amount of enalapril or a pharmaceutically acceptable salt or solvate thereof is about 10 to about 25% (w/w of solids). In some embodiments, the amount of sucralose is about 8 to about 18 (w/w of solids). In some embodiments, the amount of citric acid in the buffer is about 17 to about 47% (w/w of solids). In some embodiments, the amount of sodium citrate dihydrate in the buffer is about 1 to about 11% (w/w of solids). In some embodiments, the amount of sodium benzoate is about 12 to about 25% (w/w of solids). In some embodiments, the pH of the formulation is between about 3 and about 3.5. In some embodiments, the pH of the formulation is about 3.3. In some embodiments, the citrate concentration in the buffer is about 5 nM to about 20 mM. In some embodiments, the citrate concentration in the buffer is about 10 mM. In some embodiments, the formulation is stable at about 5±3° C. for at least 18 months. In some embodiments, the formulation is stable at about 5±3° C. for at least 24 months. In some embodiments, the formulation does not contain mannitol. In some embodiments, the formulation does not contain silicon dioxide.

In one aspect, the enalapril oral liquid formulation, comprises (i) about 1 mg/ml enalapril maleate; (ii) about 0.70 mg/ml of a sweetener that is sucralose; (iii) a buffer comprising about 1.82 mg/ml citric acid; (iv) about 1 mg/ml of a preservative that is sodium benzoate; and (v) water; wherein the pH of the formulation is less than about 3.5; and wherein the formulation is stable at about 5±3° C. for at least 12 months.

In some embodiments, the formulation further comprises a flavoring agent. In some embodiments, the buffer further comprises about 0.15 mg/mL sodium citrate dihydrate. In some embodiments, the pH of the formulation is between about 3 and about 3.5. In some embodiments, the pH of the formulation is about 3.3. In some embodiments, the citrate concentration in the buffer is about 5 mM to about 20 mM. In some embodiments, the citrate concentration in the buffer is about 10 mM. In some embodiments, the formulation is stable at about 5±3° C. for at least 18 months. In some embodiments, the formulation is stable at about 5±3° C. for at least 24 months. In some embodiments, the formulation does not contain mannitol. In some embodiments, the formulation does not contain silicon dioxide.

In one aspect, the enalapril oral liquid formulation comprises (i) about 19.3% (w/w of solids) enalapril maleate; (ii) about 13.5% (w/w of solids) of a sweetener that is sucralose; (iii) a buffer comprising about 35.2% (w/w of solids) citric acid; (iv) about 19.3% (w/w of solids) of a preservative that is sodium benzoate; and (v) water; wherein the pH of the formulation is less than about 3.5; and wherein the formulation is stable at about 5±3° C. for at least 12 months.

In some embodiments, the formulation further comprises a flavoring agent. In some embodiments, the buffer further comprises about 2.9% (w/w of solids) sodium citrate dihydrate. In some embodiments, the pH of the formulation is between about 3 and about 3.5. In some embodiments, the pH of the formulation is about 3.3. In some embodiments, the citrate concentration in the buffer is about 5 mM to about 20 mM. In some embodiments, the citrate concentration in the buffer is about 10 mM. In some embodiments, the formulation is stable at about 5±3° C. for at least 18 months. In some embodiments, the formulation is stable at about 5±3° C. for at least 24 months. In some embodiments, the formulation does not contain mannitol. In some embodiments, the formulation does not contain silicon dioxide.

In one aspect, the enalapril oral liquid formulation consists essentially of (i) about 1 mg/ml enalapril maleate; (ii) about 0.70 mg/ml of a sweetener that is sucralose; (iii) a buffer comprising about 1.82 mg/ml citric acid and about 0.15 mg/ml sodium citrate dihydrate; (iv) about 1 mg/ml of a preservative that is sodium benzoate; (v) a flavoring agent; and (vi) water; wherein the pH of the formulation is less than about 3.5 adjusted by sodium hydroxide or hydrochloric acid; and wherein the formulation is stable at about 5±3° C. for at least 12 months.

Also provided herein are methods of treating hypertension in a subject comprising administering to that subject a therapeutically effective amount of enalapril oral liquid formulation comprising (i) about 1 mg/ml enalapril maleate; (ii) about 0.7 mg/ml sucralose; (iii) a buffer comprising about 1.82 mg/ml citric acid and about 0.15 mg/ml sodium citrate dihydrate; (iv) about 1 mg/ml of a preservative that is sodium benzoate; and (v) water, wherein the pH of the formulation is less than about 3.5; and wherein the formulation is stable at about 5±3° C. for at least 12 months. In some embodiments, the formulation does not contain mannitol. In some embodiments, the formulation does not contain silicon dioxide.

In some embodiments, the hypertension is primary (essential) hypertension. In some embodiments, the hypertension is secondary hypertension. In some embodiments, the subject has blood pressure values greater than or equal to 140/90 mmm Hg. In some embodiments, the subject is an adult. In some embodiments, the subject is elderly. In some embodiments, the subject is a child. In some embodiments, the formulation is administered to the subject in a fasted state. In some embodiments, the formulation is administered to the subject in a fed state. In some embodiments, the formulation is further administered in combination with an agent selected from the group consisting of diuretics, beta blockers, alpha blockers, mixed alpha and beta blockers, calcium channel blockers, angiotensin II receptor antagonists, ACE inhibitors, aldosterone antagonists, and alpha-2 agonists.

Also provided herein are methods of treating prehypertension in a subject comprising administering to that subject a therapeutically effective amount of enalapril oral liquid formulation comprising (i) about 1 mg/ml enalapril maleate; (ii) about 0,7 mg/ml of a sweetener that is sucralose; (ii) a buffer comprising about 1.82 mg/ml citric acid and about 0.15 mg/ml sodium citrate dihydrate; (iv) about 1 mg/ml of a preservative that is sodium benzoate; and (v) water; wherein the pH of the formulation is less than about 3.5; and wherein the formulation is stable at about 5±3° C. for at least 12 months. In some embodiments, the formulation does not contain mannitol. In some embodiments, the formulation does not contain silicon dioxide.

In some embodiments, the subject has blood pressure values of about 120-139/80-89 mm Hg.

Also provided herein are methods of treating heart failure in a subject comprising administering to that subject a therapeutically effective amount of enalapril oral liquid formulation comprising (i) about 1 mg/ml enalapril maleate; (ii) about 0.70 mg/ml of a sweetener that is sucralose; a buffer comprising about 1.82 mg/ml citric acid and about 0.15 mg/ml sodium citrate dihydrate; (iv) about 1 mg/ml of a preservative that is sodium benzoate; and (v) water; wherein the pH of the formulation is less than about 3.5; and wherein the formulation is stable at about 5±3° C. for at least 12 months. In some embodiments, the formulation does not contain mannitol. In some embodiments, the formulation does not contain silicon dioxide.

Also provided herein are methods of treating left ventricular dysfunction in a subject comprising administering to that subject a therapeutically effective amount of enalapril oral liquid formulation comprising (i) about 1 mg/ml enalapril maleate; (ii) about 0.7 mg/ml of a sweetener that is sucralose; (iii) a buffer comprising about 1.82 mg/ml citric acid and about 0.15 mg/ml sodium citrate dihydrate; (iv) about 1 mg/ml of a preservative that is sodium benzoate; and (v) water; wherein the pH of the formulation is less than about 3.5; and wherein the formulation is stable at about 5±3° C. for at least 12 months. In some embodiments, the formulation does not contain mannitol. In some embodiments, the formulation does not contain silicon dioxide.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
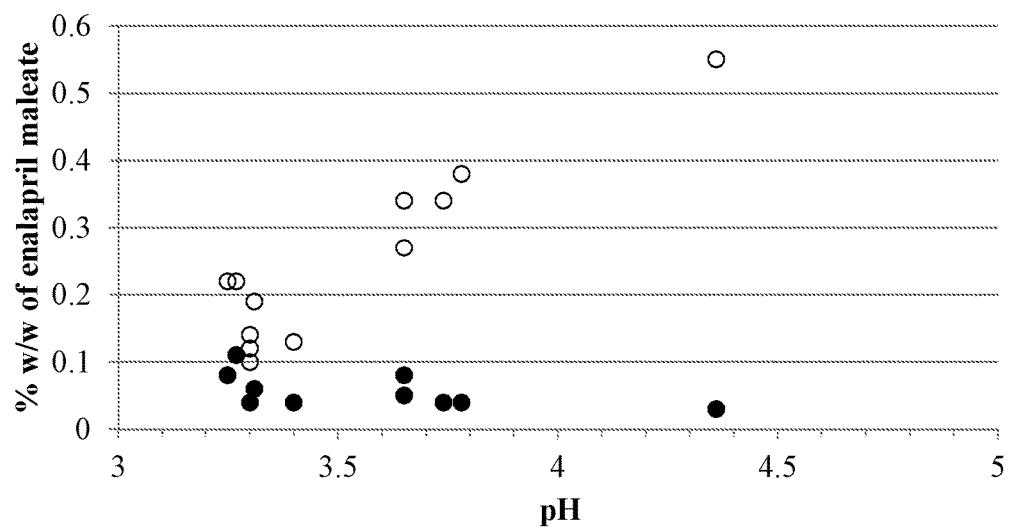
FIG. 1: Effect of pH on degradant formation after 8 weeks of storage of various enalapril solution formulations at 5° C.

Provided herein are stable enalapril oral liquid formulations. Also provided herein are stable enalapril powder formulations for reconstitution for oral liquid administration. These enalapril formulations described herein are useful for the treatment of hypertension, prehypertension, heart failure as well as ventricular dysfunction. The formulations are advantageous over conventional solid dosage administration of enalapril ranging from ease of administration, accuracy of dosing, accessibility to additional patient populations such as to children and the elderly, and an increased patient compliance to medication.

It is generally known that certain segments of the population have difficulty ingesting and swallowing solid oral dosage forms such as tablets and capsules. As many as a quarter of the total population has this difficulty. Often, this leads to non-compliance with the recommended medical therapy with the solid dosage forms, thereby resulting in rending the therapy ineffective. Further, solid dosage forms are not recommended for children or elderly due to increased risk in choking.

Furthermore, the dose of enalapril to be given to children is calculated according to the child's weight. When the calculated dose is something other than the amount present in one or more intact solid dosage forms, the solid dosage form must be divided to provide the correct dose. This leads to inaccurate dosing when solid dosages forms, such as tablets, are compounded to prepare other formulations for children.

For enalapril, one solution to overcoming the use of the tablet form is for a compounding pharmacist to pulverize and crush the enalapril tablet(s) into a powder via mortar and pestle and reconstitute the powder in some liquid form. However forming a enalapril oral liquid in this fashion has significant drawbacks including large variability in the actual dosage, incomplete solubilizing of the enalapril tablet in the liquid, rapid instability, inconsistent formulation methods per compounding pharmacy, and a number of other potential issues. The crushed tablet liquid formulation may also be potentially unsafe due to contamination with residual drugs and other substances from the mortar and pestle or other crushing agent.

Alternatively, enalapril is formulated as enalapril powder compositions for reconstitution as oral liquids as described in U.S. Pat. No. 8,568,747. The powder compositions as described in this patent require mannitol and colloidal silicon dioxide for stability and dissolution. While these powder compositions are an improvement over crushing tablets, they still require a step of mixing with a diluent. The stable enalapril oral liquid formulations described herein require no extra steps or manipulation prior to administration to a subject. Further, the stable enalapril oral liquid formulations described herein do not require or need mannitol or colloidal silicon dioxide for stability and dissolution.

The present embodiments described herein provide a safe and effective oral administration of enalapril for the treatment of hypertension and other disorders. In particular, the embodiments provide stable enalapril oral liquid formulations as well as alternatively enalapril powder formulations for oral liquid administration.

As used herein, "enalapril" refers to enalapril base, its salt, or solvate or derivative or isomer or polymorph thereof. Suitable compounds include the free base, the organic and inorganic salts, isomers, isomer salts, solvates, polymorphs, complexes etc. U.S. Pat. Nos. 4,374,829; 4,472,380 and 4,510,083 disclose exemplary methods in the preparation of enalapril. In some embodiments, the enalapril used in the formulations described herein is an enalapril salt. In some instances, the enalapril salt is enalapril maleate. In other instances, the enalapril salt is in the form of enalapril sodium.

Other ACE inhibitors are contemplated in the formulations within and include but are not limited to quinapril, indolapril, ramipril, perindopril, lisinopril, benazepril, imidapril, zofenopril, trandolapril, fosinopril, captopril, and their salts, solvates, derivatives, polymorphs, or complexes, thereof.

Enalapril Oral Liquid Formulations

Oral liquids include, but are not limited to, solutions (both aqueous and nonaqueous), suspensions, emulsions, syrups, slurries, juices, elixirs, dispersions, and the like. It is envisioned that solution/suspensions are also included where certain components described herein are in a solution while other components are in a suspension.

In one aspect, the enalapril liquid formulations described herein comprise enalapril, a preservative, a sweetening agent, a buffer, and water. In one embodiment, the sweetening agent is sucralose. In one embodiment, the sweetening agent is xylitol. In one embodiment, the sweetening agent is not mannitol. In another embodiment, the preservative is sodium benzoate. In some embodiments, the preservative is a paraben. In some embodiments, the preservative is a mixture of parabens. In yet another embodiment, the buffer comprises citric acid. In some embodiments, the buffer further comprises sodium citrate. In one aspect, the enalapril liquid formulation described herein comprises enalapril, sucralose, sodium benzoate, citric acid, sodium citrate, and water. In some embodiments, the enalapril liquid formulation herein further comprises a flavoring agent. In some embodiments, the enalapril liquid formulation is not obtained from crushing enalapril tablet and dissolving the powder in a suitable vehicle for oral administration. In some embodiments, the enalapril liquid formulation does not contain silicon dioxide. In some embodiments, the enalapril liquid formulation does not contain mannitol. In some embodiments, the enalapril liquid formulation does not contain lactose. In some embodiments, the enalapril liquid formulation does not contain magnesium stearate. In some embodiments, the enalapril liquid formulation does not contain sodium bicarbonate. In some embodiments, the enalapril liquid formulation does not contain iron oxides.

In some embodiments, enalapril or a pharmaceutically acceptable salt thereof, is present in about 0.6 to about 1.2 mg/ml in the oral liquid formulation. In other embodiments, enalapril or a pharmaceutically acceptable salt thereof, is present in about 0.6 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.7 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, about 1 mg/ml, about 1.01 mg/ml, about 1.02, mg/ml, about 1.03 mg/ml, about 1.04 mg/ml, about 1.05 mg/ml, about 1.06 mg/ml, about 1.07 mg/ml, about 1.08 mg/ml, about 1.09 mg/ml, about 1.1 mg/ml, about 1.11 mg/ml, about 1.12, mg/ml, about 1.13 mg/ml, about 1.14 mg/ml, about 1.15 mg/ml, about 1.16 mg/ml, about 1.17 mg/ml, about 1.18 mg/ml, about 1.19 mg/ml, or about 1.2 mg/ml in the liquid oral formulation. In some embodiments, enalapril is present in about 0.76 mg/ml in the oral liquid formulation. In some embodiments, enalapril maleate is present in about 1 mg/ml in the oral liquid formulation. In some embodiments, the formulation contains enalapril or another pharmaceutically acceptable salt of enalapril in a molar concentration equivalent to 1 mg/ml, enalapril maleate. In some embodiments, the formulation contains enalapril or another pharmaceutically acceptable salt of enalapril in a molar concentration equivalent to 0.76 mg/mL enalapril.

In some embodiments, enalapril or a pharmaceutically acceptable salt thereof, is present in about 0.5% w/w to about 30% w/w of the solids in the oral liquid formulation. In other embodiments, enalapril or a pharmaceutically acceptable salt thereof, is present in about 0.5% w/w, about 1% w/w, about 1.5% w/w, about 2% w/w, about 2.5% w/w, about 3% w/w, about 3.5% w/w, about 4% w/w, about 4.5% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, about 10% w/w, about 10.5% w/w, about 11% w/w, about 11.5% w/w, about 12% w/w, about 12.5% w/w, about 13% w/w, about 13.5% w/w, about 14% w/w, about 14.5% w/w, about 15% w/w, about 15.1% w/w, about 15.2% w/w, about 15.3% w/w, about 15.4% w/w, about 15.5% w/w, about 15.6% w/w, about 15.7% w/w, about 15.8% w/w, about 15.9% w/w, about 16% w/w, about 16.1% w/w, about 16.2% w/w, about 16.3% w/w, about 16.4% w/w, about 16.5% w/w, about 16.6% w/w, about 16.7% w/w, about 16.8% w/w, about 16.9% w/w, about 17% w/w, about 17.1% w/w, about 17.2% w/w, about 17.3% w/w, about 17.4 w/w, about 17.5% w/w, about 17.6% w/w, about 17.7% w/w, about 17.8% w/w, about 17.9% w/w, about 18% w/w, about 18.1% w/w, about 18.2% w/w, about 18.3% w/w, about 18.4% w/w, about 18.5 w/w, about 18.6% w/w, about 18.7% w/w, about 18.8% w/w, about 18.9% w/w, about 19% w/w, about 19.1% w/w, about 19.2% w/w, about 19.3% w/w, about 19.4% w/w, about 19.5% w/w, about 19.6% w/w, about 19.7% w/w, about 19.8% w/w, about 19.9% w/w, about 20% w/w, about 20.1% w/w, about 20.2% w/w, about 20.3% w/w, about 20.4% w/w, about 20.5% w/w, about 20.6% w/w, about 20.7% w/w, about 20.8% w/w, about 20.9% w/w, about 21% w/w, about 21.1% w/w, about 21.2 w/w, about 21.3% w/w, about 21.4% w/w, about 21.5% w/w, about 21.6% w/w, about 21.7% w/w, about 21.8% w/w, about 21.9% w/w, about 22% w/w, about 22.5% w/w, about 23% w/w, about 23.5% w/w, about 24% w/w, about 24.5% w/w, about 25% w/w, about 25.5% w/w, about 26% w/w, about 26.5% w/w, about 27% w/w, about 27.5% w/w, about 28% w/w, about 28.5% w/w, about 29% w/w, about 29.5% w/w, or about 30% w/w of the solids in the oral liquid formulation. In some embodiments, enalapril or a pharmaceutically acceptable salt thereof, is present in about 10% w/w to about 25% w/w of the solids in the oral liquid formulation. In some embodiments, enalapril is present in about 10.5% w/w of the solids in the oral liquid formulation. In some embodiments, enalapril is present in about 15% w/w of the solids in the oral liquid formulation. In some embodiments, enalapril is present in about 18.2 w/w of the solids in the oral liquid formulation. In some embodiments, enalapril maleate is present in about 13.5% w/w of the solids in the oral liquid formulation. In some embodiments, enalapril maleate is present in about 19.3% w/w of the solids in the oral liquid formulation. In some embodiments, enalapril maleate is present in about 24.5% w/w of the solids in the oral liquid formulation.

In some embodiments, enalapril or a pharmaceutically acceptable salt thereof, is present in about 0.1% w/w to about 1% w/w of the solids in the oral liquid formulation. In other embodiments, enalapril or a pharmaceutically acceptable salt thereof, is present in about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, or about 1% w/w of the solids in the oral liquid formulation. In some embodiments, enalapril or a pharmaceutically acceptable salt thereof, is present in about 0.4% w/w to about 0.7% w/w of the solids in the oral liquid formulation. In some embodiments, enalapril is present in about 0.4% w/w of the solids in the oral liquid formulation. In some embodiments, enalapril is present in about 0.5% w/w of the solids in the oral liquid formulation. In some embodiments, enalapril maleate is present in about 0.5% w/w of the solids in the oral liquid formulation. In some embodiments, enalapril maleate is present in about 0.6% w/w of the solids in the oral liquid formulation.

Sweetener in the Enalapril Oral Liquid Formulations

Sweeteners or sweetening agents include any compounds that provide a sweet taste. This includes natural and synthetic sugars, natural and artificial sweeteners, natural extracts and any material that initiates a sweet sensation in a subject. In some embodiments, a solid/powder sweetener is used in the oral liquid formulation described herein. In other embodiments, a liquid sweetener is used in the oral liquid formulation described herein.

Sugars illustratively include glucose, fructose, sucrose, xylitol, tagatose, sucralose, maltitol, isomaltulose, Isomalt™ (hydrogenated isomaltulose), lactitol, sorbitol, erythritol, trehalose, maltodextrin, polydextrose, and the like. Other sweeteners illustratively include glycerin, inulin, erythritol, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrolysates, maltitol syrup, high fructose corn syrup, etc., and as branded products, e.g., Sweet Am™ liquid (Product Code 918.003-propylene glycol, ethyl alcohol, and proprietary artificial flavor combination, Flavors of North America) and Sweet Am™ powder (Product Code 918.005—maltodextrin, sorbitol, and fructose combination and Product Code 918.010—water, propylene glycol, sorbitol, fructose, and proprietary natural and artificial flavor combination, Flavors of North America), ProSweet™ (1-10% proprietary plant/vegetable extract and 90-99% dextrose combination, Viriginia Dare), Maltisweet™ (maltitol solution, Ingredion), Sorbo™ (sorbitol and sorbitol/xylitol solution, SPI Polyols), Invertose™ (high fructose corn syrup, Ingredion), Rebalance M60 and X60 (sucralose and maltodextrin, Tate and Lyle), and Ora-Sweet® sugar-free flavored syrup (Paddock Laboratories, Inc.). Sweeteners can be used singly or in combinations of two or more. Suitable concentrations of different sweeteners can be selected based on published information, manufacturers' data sheets and by routine testing.

In some embodiments, the enalapril oral liquid formulation described herein comprises a sweetening agent. In some embodiments, the sweetening agent is sucralose. In some embodiments, the sweetening agent is xylitol. In some embodiments, the sweetener is not mannitol.

In some embodiments, the enalapril oral liquid formulation described herein comprises sucralose. In some embodiments, sucralose is present in about 0.5 to about 0.9 mg/ml in the oral liquid formulation. In other embodiments, sucralose is present in about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.60 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.70 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.80 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, or about 0.90 mg/ml in the oral liquid formulation. In some embodiments, sucralose is present in about 0.7 mg/ml in the oral liquid formulation.

In some embodiments, sucralose is present in about 1% w/w to about 30% w/w of the solids in the oral liquid formulation. In some embodiments, sucralose is present in about 1% w/w, about 1.5% w/w, about 2% w/w, about 2.5% w/w, about 3% w/w, about 3.5% w/w, about 4% w/w, about 4.5% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, about 10% w/w, about 10.5% w/w, about 11% w/w, about 11.5% w/w, about 12% w/w, about 12.5% w/w, about 13% w/w, about 13.5% w/w, about 14% w/w, about 14.5% w/w, about 15% w/w, about 15.5% w/w, about 16% w/w, about 16.5% w/w, about 17% w/w, about 17.5% w/w, about 18% w/w, about 18.5% w/w, about 19% w/w, about 19.5% w/w, about 20% w/w, about 20.5% w/w, about 21% w/w, about 21.5% w/w, about 22% w/w, about 22.5% w/w, about 23% w/w, about 23.5% w/w, about 24% w/w, about 24.5% w/w, about 25% w/w, about 25.5% w/w, about 26% w/w, about 26.5% w/w, about 27% w/w, about 27.5% w/w, about 28% w/w, about 28.5% w/w, about 29% w/w, about 29.5% w/w, or about 30% w/w of the solids in the oral liquid formulation. In some embodiments, sucralose is present in about 8% w/w to about 18% w/w of the solids in the oral liquid formulation. In some embodiments, sucralose is present in about 9.5% w/w of the solids in the oral liquid formulation. In some embodiments, sucralose is present in about 13.5% w/w of the solids in the oral liquid formulation. In some embodiments, sucralose is present in about 16.5% w/w of the solids in the oral liquid formulation.

In some embodiments, the enalapril oral liquid formulation described herein comprises xylitol. In some embodiments, xylitol is present in about 140 mg/ml to about 210 mg/ml in the oral liquid formulation.

In some embodiments, xylitol is present in about 140 mg/ml, about 145 mg/ml, about 150 mg/ml, about 155 mg/ml, about 160 mg/ml, about 165 mg/ml, about 170 mg/ml, about 175 mg/ml, about 180 mg/ml, about 185 mg/ml, about 190 mg/ml, about 195 mg/ml, about 200 mg/ml, about 205 mg/ml, or about 210 mg/ml of the oral liquid formulation. In some embodiments, xylitol is present in about 150 mg/ml in the oral liquid formulation. In some embodiments, xylitol is present in about 200 mg/ml in the oral liquid formulation.

In some embodiments, xylitol is present in about 80% w/w to about 99% w/w of the solids in the oral liquid formulation. In other embodiments, xylitol is present in about 80% w/w, about 81% w/w, about 82% w/w, about 83% w/w, about 84% w/w, about 85% w/w, about 86% w/w, about 87% w/w, about 88% w/w, about 89% w/w, about 90% w/w, about 91% w/w, about 92% w/w, about 93% w/w, about 94% w/w, about 95% w/w, about 96% w/w, about 97% w/w, about 98% w/w, or about 99% w/w of the solids in the oral liquid formulation. In some embodiments, xylitol is present in about 96% w/w to about 98% w/w of the solids in the oral liquid formulation. In some embodiments, xylitol is present in about 96% w/w of the solids in the oral liquid formulation.

Preservative in the Enalapril Oral Liquid Formulations

Preservatives include anti-microbials, anti-oxidants, and agents that enhance sterility. Exemplary preservatives include ascorbic acid, ascorbyl palmitate, BHA, BHT, citric acid, EDTA and its salts, erythorbic acid, fumaric acid, malic acid, propyl gallate, sodium ascorbate, sodium bisulfate, sodium metabisulfite, sodium sulfite, parabens (such as methylparaben, ethylparaben, propylparaben, butylparaben and their salts), benzoic acid, sodium benzoate, potassium sorbate, vanillin, and the like.

In some embodiments, the enalapril oral liquid formulation described herein comprises a preservative.

In some embodiments, the preservative is a paraben and the sweetener is not a sugar (such as, but not limited to glucose, fructose, sucrose, lactose, maltose) or a sugar alcohol (such as, but not limited to xylitol, mannitol, lactitol, maltitol, sorbitol).

In some embodiments, the preservative is sodium benzoate.

In some embodiments, modulation of the pH is desired to provide the best antimicrobial activity of the preservative, sodium benzoate. In some embodiments, the antimicrobial activity of sodium benzoate drops when the pH is increased above 5.

In some embodiments, the pH of the enalapril oral liquid formulation described herein is less than about 4. In some embodiments, the pH of the enalapril oral liquid formulation described herein is less than about 3.5. In some embodiments, the pH of the enalapril oral liquid formulation described herein is between about 3 and about 4. In some embodiments, the pH of the enalapril oral liquid formulation described herein is between about 3 and about 3.5. In some embodiments, the pH of the enalapril oral liquid formulation described herein is about 3, about 3.1, about 3.2, about 3.3, about 3.4, about 3.5, about 3.6, about 3.7, about 3.8, about 3.9, or about 4. In some embodiments, the pH of the enalapril oral liquid formulation described herein is about 3.3.

In some embodiments, sodium benzoate is present in about 0.2 to about 1.2 mg/ml in the oral liquid formulation. In other embodiments, sodium benzoate is present in about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, about 0.3 mg/ml, about 0.31 mg/ml, about 0.32 mg/ml, about 0.33 mg/ml, about 0.34 mg/ml, about 0.35 mg/ml, about 0.36 mg/ml, about 0.37 mg/ml, about 0.38 mg/ml, about 0.39 mg/ml, about 0.4 mg/ml, about 0.41 mg/ml, about 0.42 mg/ml, about 0.43 mg/ml, about 0.44 mg/ml, about 0.45 mg/ml, about 0.46 mg/ml, about 0.47 mg/ml, about 0.48 mg/ml, about 0.49 mg/ml, about 0.5 mg/ml, about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.6 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.7 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, about 1 mg/ml, about 1.01 mg/ml, about 1.02, mg/ml, about 1.03 mg/ml, about 1.04 mg/ml, about 1.05 mg/ml, about 1.06 mg/ml, about 1.07 mg/ml, about 1.08 mg/ml, about 1.09 mg/ml, about 1.1 mg/ml, about 1.11 mg/ml, about 1.12, mg/ml, about 1.13 mg/ml, about 1.14 mg/ml, about 1.15 mg/ml, about 1.16 mg/ml, about 1.17 mg/ml, about 1.18 mg/ml, about 1.19 mg/ml, or about 1.2 mg/ml in the liquid oral formulation. In some embodiments, sodium benzoate is present in about 1 mg/ml in the oral liquid formulation.

In some embodiments, sodium benzoate is present in about 1% w/w to about 30% w/w of the solids in the oral liquid formulation. In other embodiments, sodium benzoate is present in about 1% w/w, about 1.5% w/w, about 2% w/w, about 2.5% w/w, about 3% w/w, about 3.5% w/w, about 4% w/w, about 4.5% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, about 10% w/w, about 10.5% w/w, about 11% w/w, about 11.5% w/w, about 12% w/w, about 12.5% w/w, about 13% w/w, about 13.5% w/w, about 14% w/w, about 14.5% w/w, about 15% w/w, about 15.1% w/w, about 15.2% w/w, about 15.3% w/w, about 15.4% w/w, about 15.5% w/w, about 15.6% w/w, about 15.7% w/w, about 15.8% w/w, about 15.9% w/w, about 16% w/w, about 16.1% w/w, about 16.2% w/w, about 16.3% w/w, about 16.4% w/w, about 16.5% w/w, about 16.6% w/w, about 16.7% w/w, about 16.8% w/w, about 16.9% w/w, about 17% w/w, about 17.1% w/w, about 17.2% w/w, about 17.3% w/w, about 17.4% w/w, about 17.5% w/w, about 17.6% w/w, about 17.7% w/w, about 17.8% w/w, about 17.9% w/w, about 18% w/w, about 18.1% w/w, about 18.2% w/w, about 18.3% w/w, about 18.4% w/w, about 18.5% w/w, about 18.6% w/w, about 18.7% w/w, about 18.8% w/w, about 18.9% w/w, about 19% w/w, about 19.1% w/w, about 19.2% w/w, about 19.3% w/w, about 19.4% w/w, about 19.5% w/w, about 19.6% w/w, about 19.7% w/w, about 19.8% w/w, about 19.9% w/w, about 20% w/w, about 20.1% w/w, about 20.2% w/w, about 20.3% w/w, about 20.4% w/w, about 20.5% w/w, about 20.6% w/w, about 20.7% w/w, about 20.8% w/w, about 20.9% w/w, about 21% w/w, about 21.1% w/w, about 21.2% w/w, about 21.3% w/w, about 21.4% w/w, about 21.5% w/w, about 21.6% w/w, about 21.7% w/w, about 21.8% w/w, about 21.9% w/w, about 22% w/w, about 22.5% w/w, about 23% w/w, about 23.5% w/w, about 24% w/w, about 24.5% w/w, about 25% w/w, about 25.5% w/w, about 26% w/w, about 26.5% w/w, about 27% w/w, about 27.5% w/w, about 28% w/w, about 28.5% w/w, about 29% w/w, about 29.5% w/w, or about 30% w/w of the solids in the oral liquid formulation. In some embodiments, sodium benzoate is present in about 10% w/w to about 25% w/w of the solids in the oral liquid formulation. In some embodiments, sodium benzoate is present in about 13.5% w/w of the solids in the oral liquid formulation. In some embodiments, sodium benzoate is present in about 19.3% w/w of the solids in the oral liquid formulation. In some embodiments, sodium benzoate is present in about 23.5% w/w of the solids in the oral liquid formulation.

In some embodiments, sodium benzoate is present in about 0.1% w/w to about 1% w/w of the solids in the oral liquid formulation. In other embodiments, sodium benzoate is present in about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, or about 1% w/w of the solids in the oral liquid formulation. In some embodiments, sodium benzoate is present in about 0.4% w/w to about 0.7% w/w of the solids in the oral liquid formulation. In some embodiments, sodium benzoate is present in about 0.45% w/w of the solids in the oral liquid formulation. In some embodiments, sodium benzoate is present in about 0.6% w/w of the solids in the oral liquid formulation.

In some embodiments, sodium benzoate is present in an amount sufficient to provide antimicrobial effectiveness to the enalapril oral liquid formulation described herein. (See Table G-1).

In some embodiments, the preservative is a paraben. In some embodiments, the preservative is a mixture of parabens. In some embodiments, the paraben or mixture of parabens is present in about 0.1 mg/ml to about 2 mg/ml in the oral liquid formulation. In other embodiments, the paraben or mixture of parabens is present in about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1 mg/ml, about 1.1 mg/ml, about 1.2 mg/ml, about 1.3 mg/ml, about 1.4 mg/ml, or about 1.5 mg/ml, about 1.6 mg/ml, about 1.7 mg/ml, about 1.8 mg/ml, about 1.9 mg/ml, or about 2 mg/ml in the liquid oral formulation. In some embodiments, the paraben or mixture of parabens is present in about 1.6 mg/ml to about 2 mg/ml in the oral liquid formulation. In some embodiments, the paraben or mixture of parabens is present in about 1.6 mg/ml to about 1.8 mg/ml in the oral liquid formulation. In some embodiments, the paraben or mixture of parabens is present in about 0.1 mg/ml to about 0.5 mg/ml in the oral liquid formulation.

In some embodiments, the paraben or mixture of parabens is present in about 2% w/w to about 30% w/w of the solids in the oral liquid formulation. In other embodiments, the paraben or mixture of parabens is present in about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, or about 30% w/w of the solids in the oral liquid formulation. In some embodiments, the paraben or mixture of parabens is present in about 2% w/w to about 3% w/w of the solids in the oral liquid formulation. In some embodiments, the paraben or mixture of parabens is present in about 23% w/w to about 26% w/w of the solids in the oral liquid formulation. In some embodiments, the paraben or mixture of parabens is present in about 26% w/w to about 30% w/w of the solids in the oral liquid formulation.

Sweetener and preservative incompatibility

Paraben preservatives (especially methylparaben) can react with selected sugars (glucose, fructose, sucrose, lactose, maltose) and sugar alcohols (xylitol, mannitol, lactitol, maltitol, sorbitol) to form transesterification reaction products. This can be undesirable from a formulation and stability standpoint as the transesterification creates additional degradants.

In some embodiments, the enalapril oral liquid formulation described herein does not comprise a paraben preservative. In further embodiments, the enalapril oral liquid formulation described herein does not comprise a paraben preservative when the formulation also comprises a sugar or sugar alcohol.

pH of Enalapril Oral Liquid Formulations

Buffering agents maintain the pH of the liquid enalapril formulation. Non-limiting examples of buffering agents include, but are not limited to sodium bicarbonate, potassium bicarbonate, magnesium hydroxide, magnesium lactate, magnesium glucomate, aluminum hydroxide, aluminum hydroxide/sodium bicarbonate co-precipitate, mixture of an amino acid and a buffer, a mixture of aluminum glycinate and a buffer, a mixture of an acid salt of an amino acid and a buffer, and a mixture of an alkali salt of an amino acid and a buffer. Additional buffering agents include citric acid, sodium citrate, sodium tartarate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts. Some buffering agents also impart effervescent qualities when a powder is reconstituted in a solution. In some embodiments, the buffering agent is not sodium bicarbonate.

In some embodiments, the oral liquid formulation comprises a buffer.

In some embodiments, the buffer in the enalapril oral liquid formulation described herein comprises citric acid. In some embodiments, the buffer in the enalapril oral liquid formulation described herein comprises citric acid and sodium citrate. In some embodiments, the buffer in the enalapril oral liquid formulation described herein comprises citric acid and sodium citrate dihydrate or an equivalent molar amount of sodium citrate anhydrous. hi some embodiments, the sodium citrate is monosodium citrate. In some embodiments, the sodium citrate is disodium citrate. In some embodiments, the sodium citrate is trisodium citrate.

In some embodiments, the buffer in the enalapril oral liquid formulation described herein comprises phosphoric acid. In some embodiments, the buffer in the enalapril oral liquid formulation described herein comprises sodium phosphate.

In some embodiments, modulation of the pH is desired to provide a lowered impurity profile. In the exemplary stability studies, the main enalapril degradants are enalapril diketopiperazine and enalaprilat:

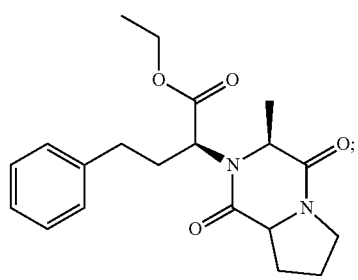

enalapril diketopiperazine

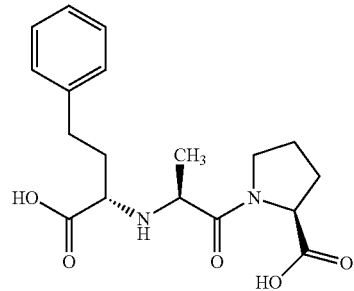

enalaprilat

In some embodiments, the percentage of enalaprilat formation is increased when the pH is above 3.5. (See table C-2 and FIG. 1 and FIG. 2). In some embodiments, the percentage of enalapril diketopiperazine formation is slightly increased as the pH is below 4.

In some embodiments, the pH of the enalapril oral liquid formulation described herein is less than about 4. In some embodiments, the pH of the enalapril oral liquid formulation described herein is less than about 3.5. In some embodiments, the pH of the enalapril oral liquid formulation described herein is between about 3 and about 4. In some embodiments, the pH of the enalapril oral liquid formulation described herein is between about 3 and about 3.5. In some embodiments, the pH of the enalapril oral liquid formulation described herein is about 3, about 3.1, about 3.2, about 3.3, about 3.4, about 3.5, about 3.6, about 3.7, about 3.8, about 3.9, or about 4. In some embodiments, the pH of the enalapril oral liquid formulation described herein is about 3.3.

In some embodiments, the formation of degradants is dependent on the buffer concentration. In some embodiments, the buffer concentration impacts the taste of the enalapril oral liquid formulation.

In some embodiments, the buffer concentration is between about 5 mM and about 20 mM. In some embodiments, the buffer concentration is about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM. In some embodiments, the buffer concentration is about 5 mM. In some embodiments, the buffer concentration is about 10 mM. In some embodiments, the buffer concentration is about 20 mM.

In some embodiments, citric acid is present in about 0.7 to about 2 mg/ml in the oral liquid formulation. In other embodiments, citric acid is present in about 0.7 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/mL, about 0.91 mg/mL, about 0.92 mg/mL, about 0.93 mg/mL, about 0.94 mg/mL, about 0.95 mg/mL, about 0.96 mg/mL, about 0.97 mg/mL, about 0.98 mg/mL, about 0.99 mg/mL, about 1 mg/mL, about 1.11 mg/ml, about 1.12 mg/ml, about 1.13 mg/ml, about 1.14 mg/ml, about 1.15 mg/ml, about 1.16 mg/ml, about 1.17 mg/ml, about 1.18 mg/ml, about 1.19 mg/ml, about 1.2 mg/ml, about 1.21 mg/ml, about 1.22 mg/ml, about 1.23 mg/ml, about 1.24 mg/ml, about 1.25 mg/ml, about 1.26 mg/ml, about 1.27 mg/ml, about 1.28 mg/ml, about 1.29 mg/ml, about 1.3 mg/mL, about 1.31 mg/mL, about 1.32 mg/mL, about 1.33 mg/mL, about 1.34 mg/mL, about 1.35 mg/mL, about 1.36 mg/mL, about 1.37 mg/mL, about 1.38 mg/mL, about 1.39 mg/mL, about 1.4 mg/ml, about 1.41 mg/ml, about 1.42 mg/ml, about 1.43 mg/ml, about 1.44 mg/ml, about 1.45 mg/ml, about 1.46 mg/ml, about 1.47 mg/ml, about 1.48 mg/ml, about 1.49 mg/ml, about 1.5 mg/ml, about 1.51 mg/ml, about 1.52 mg/ml, about 1.53 mg/ml, about 1.54 mg/ml, about 1.55 mg/ml, about 1.56 mg/ml, about 1.57 mg/ml, about 1.58 mg/ml, about 1.59 mg/ml, about 1.6 mg/mL, about 1.61 mg/mL, about 1.62 mg/mL, about 1.63 mg/mL, about 1.64 mg/mL, about 1.65 mg/mL, about 1.66 mg/mL, about 1.67 mg/mL, about 1.68 mg/mL, about 1.69 mg/mL, about 1.7 mg/ml, about 1.71 mg/ml, about 1.72 mg/ml, about 1.73 mg/ml, about 1.74 mg/ml, about 1.75 mg/ml, about 1.76 mg/ml, about 1.77 mg/ml, about 1.78 mg/ml, about 1.79 mg/ml, about 1.8 mg/ml, about 1.81 mg/ml, about 1.82 mg/ml, about 1.83 mg/ml, about 1.84 mg/ml, about 1.85 mg/ml, about 1.86 mg/ml, about 1.87 mg/ml, about 1.88 mg/ml, about 1.89 mg/ml, about 1.9 mg/mL, about 1.91 mg/mL, about 1.92 mg/mL, about 1.93 mg/mL, about 1.94 mg/mL, about 1.95 mg/mL, about 1.96 mg/mL, about 1.97 mg/mL, about 1.98 mg/mL, about 1.99 mg/mL, or about 2 mg/mL in the oral liquid formulation. In some embodiments, citric acid is present in about 1.65 mg/ml in the oral liquid formulation. In some embodiments, citric acid is present in about 1.82 mg/ml in the oral liquid formulation. In some embodiments, citric acid is present in about 0.82 mg/ml in the oral liquid formulation.

In some embodiments, citric acid is present in about 2 to about 3.5 mg/ml in the oral liquid formulation. In other embodiments, citric acid is present in about 2 mg/mL, about 2.05 mg/mL, about 2.1 mg/mL, about 2.15 mg/mL, about 2.2 mg/mL, about 2.25 mg/mL, about 2.3 mg/mL, about 2.35 mg/mL, about 2.4 mg/mL, about 2.45 mg/mL, about 2.5 mg/mL, about 2.55 mg/mL, about 2.6 mg/mL, about 2.65 mg/mL, about 2.7 mg/mL, about 2.75 mg/mL, about 2.8 mg/mL, about 2.85 mg/mL, about 2.9 mg/mL, about 2.95 mg/mL, about 3 mg/mL, about 3.05 mg/ml, about 3.1 mg/mL, about 3.15 mg/mL, about 3.2 mg/mL, about 3.25 mg/mL, about 3.3 mg/mL, about 3.35 mg/mL, about 3.4 mg/mL, about 3.45 mg/mL, or about 3.5 mg/mL in the oral liquid formulation. In some embodiments, citric acid is present in about 3.3 mg/ml in the oral liquid formulation.

In some embodiments, citric acid is present in about 10% w/w to about 50% w/w of the solids in the oral liquid formulation. In other embodiments, citric acid is present in about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, about 50% w/w of the solids in the oral liquid formulation. In some embodiments, citric acid is present in about 45% w/w of the solids in the oral liquid formulation. In some embodiments, citric acid is present in about 31% w/w of the solids in the oral liquid formulation. In some embodiments, citric acid is present in about 35% w/w of the solids in the oral liquid formulation. In some embodiments, citric acid is present in about 19% w/w of the solids in the oral liquid formulation.

In some embodiments, citric acid is present in about 1% w/w to about 5% w/w of the solids in the oral liquid formulation. In other embodiments, citric acid is present in about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5% w/w of the solids in the oral liquid formulation. In some embodiments, citric acid is present in about 2.1% w/w of the solids in the oral liquid formulation. In some embodiments, citric acid is present in about 1.6% w/w of the solids in the oral liquid formulation.

In some embodiments, sodium citrate dihydrate is present in about 0.1 to about 0.8 mg/ml in the oral liquid formulation. In other embodiments, sodium citrate dihydrate is present in the oral liquid formulation is about 0.1 mg/mL, about 0.11 mg/mL, about 0.12 mg/mL, about 0.13 mg/mL, about 0.14 mg/mL, about 0.15 mg/ml, about 0.16 mg/mL, about 0.17 mg/mL, about 0.18 mg/mL, about 0.19 mg/mL, about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, about 0.3 mg/ml, about 0.31 mg/ml, about 0.32 mg/ml, about 0.33 mg/ml, about 0.34 mg/ml, about 0.35 mg/ml, about 0.36 mg/ml, about 0.37 mg/ml, about 0.38 mg/ml, about 0.39 mg/ml, about 0.4 mg/ml, about 0.41 mg/ml, about 0.42 mg/ml, about 0.43 mg/ml, about 0.44 mg/ml, about 0.45 mg/ml, about 0.46 mg/ml, about 0.47 mg/ml, about 0.48 mg/ml, about 0.49 mg/ml, about 0.5 mg/ml, about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.6 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.7 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, or about 0.8 mg/ml in the oral liquid formulation. In some embodiments, sodium citrate dihydrate is present in about 0.75 mg/ml in the oral liquid formulation. In some embodiments, sodium citrate dihydrate is present in about 0.35 mg/ml in the oral liquid formulation. In some embodiments, sodium citrate dihydrate is present in about 0.2 mg/ml in the oral liquid formulation. In some embodiments, sodium citrate dihydrate is present in about 0.15 mg/ml in the oral liquid formulation.

In some embodiments, sodium citrate dihydrate is present in about 1% w/w to about 15% w/w of the solids in the oral liquid formulation. In other embodiments, sodium citrate dihydrate is present in about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.5% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, about 10% w/w, about 10.5% w/w, about 11% w/w, about 11.5% w/w, about 12% w/w, about 12.5% w/w, about 13% w/w, about 13.5% w/w, about 14% w/w, about 14.5% w/w, about 15% w/w of the solids in the oral liquid formulation. In some embodiments, sodium citrate dihydrate is present in about 10.5% w/w of the solids in the oral liquid formulation. In some embodiments, sodium citrate dihydrate is present in about 7.5% w/w of the solids in the oral liquid formulation. In some embodiments, sodium citrate dihydrate is present in about 4.5% w/w of the solids in the oral liquid formulation. In some embodiments, sodium citrate dihydrate is present in about 2.9% w/w of the solids in the oral liquid formulation.

In other embodiments, sodium citrate dihydrate is not added to the formulation.

Additional Excipients

In further embodiments, the enalapril liquid formulation described herein comprises additional excipients including, but not limited to, glidants, flavoring agents, coloring agents and thickeners. Additional excipients such as bulking agents, tonicity agents and chelating agents are within the scope of the embodiments.

Glidants are substances that improve flowability of a powder. Suitable glidants include, but are not limited to, calcium phosphate tribasic, calcium silicate, cellulose (powdered), colloidal silicon dioxide, magnesium silicate, magnesium trisilicate, silicon dioxide, starch, talc and the like. In some embodiments, the enalapril powder formulations described herein comprise a glidant. In some embodiments the glidant is not colloidal silicon dioxide.

In another embodiment, the enalapril liquid formulation comprises a flavoring agent or flavorant to enhance the taste or aroma of the formulation in liquid form. Suitable natural or synthetic flavoring agents can be selected from standard reference books, for example Fenaroli's Handbook of Flavor Ingredients, 3rd edition (1995). Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, mixed berry, orange, peach, pear, peppermint, pineapple, raspberry, rose, spearmint, strawberry, tangerine, tea, vanilla, wintergreen, etc. Also useful, particularly where the formulation is intended primarily for pediatric use, is tutti-frutti or bubblegum flavor, a compounded flavoring agent based on fruit flavors. Presently preferred flavoring agents include anise, cinnamon, cacao, orange, peppermint, cherry (in particular wild cherry), grape, bubblegum, vanilla, and mixed berry. In some embodiments, the enalapril liquid formulation described herein comprises a mixed berry flavoring agent. Flavoring agents can be used singly or in combinations of two or more.

In further embodiments, the enalapril liquid formulation comprises a coloring agent for identity and/or aesthetic purposes. Suitable coloring agents illustratively include FD&C Red No. 3, FD&C Red No. 20, FD&C Red No. 40, FD&C Yellow No. 6, FD&C Blue No. 2, FD&C Green No. 5, FD&C Orange No. 5, caramel, ferric oxide and mixtures thereof.

Thickeners impart viscosity or weight to the resultant liquid forms from the enalapril formulation described herein. Exemplary thickeners include dextrin, cellulose derivatives (carboxymethylcellulose and its salts, ethylcellulose, hydroxyethyl cellulose, methylcellulose, hypromellose, and the like) starches, pectin, polyethylene glycol, polyethylene oxide, trehalose and certain gums (xanthan gum, locust bean gum, etc.). In certain embodiments, the enalapril liquid formulation comprises a thickener.

Additional excipients are contemplated in the enalapril liquid formulation embodiments. These additional excipients are selected based on function and compatibility with the enalapril liquid formulations described herein and may be found, for example in *Remington: The Science and Practice of Pharmacy*, Nineteenth Ed (Easton, Pa.: Mack Publishing Company, 1995); Hoover, John E., *Remington's Pharmaceutical Sciences*, (Easton, Pa.: Mack Publishing Co 1975); Liberman, H.A. and Lachman, L., Eds., *Pharmaceutical Dosage Forms* (New York, N.Y.: Marcel Decker 1980); and *Pharmaceutical Dosage Forms and Drug Delivery Systems*, Seventh Ed (Lippincott Williams & Wilkins 1999), herein incorporated by reference in their entirety.

Stability

The main enalapril degradants are enalapril diketopiperazine and enalaprilat.

The enalapril oral liquid formulations described herein are stable in various storage conditions including refrigerated, ambient and accelerated conditions. Stable as used herein refers to enalapril oral liquid formulations having about 95% or greater of the initial enalapril amount and about 5% w/w or less total impurities or related substances at the end of a given storage period. The percentage of impurities is calculated from the amount of impurities relative to the amount of enalapril. Stability is assessed by HPLC or any other known testing method. In some embodiments, the stable enalapril oral liquid formulations have about 5% w/w, about 4% w/w, about 3% w/w, about 2.5% w/w, about 2% w/w, about 1.5% w/w, about 1% w/w, or about 0.5% w/w total impurities or related substances. In other embodiments, the stable enalapril oral liquid formulations have about 5% w/w total impurities or related substances. In yet other embodiments, the stable enalapril oral liquid formulations have about 4% w/w total impurities or related substances. In yet other embodiments, the stable enalapril oral liquid formulations have about 3% w/w total impurities or related substances. In yet other embodiments, the stable enalapril oral liquid formulations have about 2% w/w total impurities or related substances. In yet other embodiments, the stable enalapril oral liquid formulations have about 1% w/w total impurities or related substances.

At refrigerated condition, the enalapril oral liquid formulations described herein are stable for at least 1 month, at least 2 months, at least 3 months, at least 6 months, at least 9 months, at least 12 months, at least 15 months, at least 18 months, at least 24 months, at least 30 months and at least 36 months. In some embodiments, refrigerated condition is 5±3° C. In some embodiments, refrigerated condition is about 2° C., about 2.1° C., about 2.2° C., about 2.3° C., about 2.4° C., about 2.5° C., about 2.6° C., about 2.7 ° C., about 2.8° C., about 2.9° C., about 3° C., about 3.1° C., about 3.2° C., about 3.3° C., about 3.4° C., about 3.5° C., about 3.6° C., about 3.7° C., about 3.8° C., about 3.9° C., about 4° C., about 4.1° C., about 4.2° C., about 4.3° C., about 4.4° C., about 4.5° C., about 4.6° C., about 4.7° C., about 4.8° C., about 4.9° C., about 5° C., about 5.1° C., about 5.2° C., about 5.3° C., about 5.4° C., about 5.5° C., about 5.6° C., about 5.7° C., about 5.8° C., about 5.9° C., about 6° C., about 6.1° C., about 6.2° C., about 6.3° C., about 6.4° C., about 6.5° C., about 6.6° C., about 6.7° C., about 6.8° C., about 6.9° C., about 7° C., about 7.1° C., about 7.2° C., about 7.3° C., about 7.4° C., about 7.5° C., about 7.6° C., about 7.7° C., about 7.8° C., about 7.9° C., or about 8° C. At accelerated conditions, the enalapril oral liquid formulations described herein are stable for at least 1 month, at least 2 months, at least 3 months, at least 4 months, at least 5 months, at least 6 months, at least 7 months, at least 8 months, at least 9 months, at least 10 months, at least 11 months or at least 12 months. Accelerated conditions for the enalapril oral liquid formulations described herein include temperature and/or relative humidity (RH) that are at or above ambient levels (e.g. 25±5° C.; 55±10% RH). In some instances, an accelerated condition is at about 25° C., about 30° C., about 35° C., about 40° C., about 45° C., about 50° C., about 55° C. or about 60° C. In other instances, an accelerated condition is above 55% RH, about 65% RH, about 70% RH, about 75% RH or about 80% RH. In further instances, an accelerated condition is about 40° C. or 60° C. at ambient humidity. In yet further instances, an accelerated condition is about 40° C. at 75±5% RH humidity.

Enalapril Oral Powder Formulation

In another aspect, enalapril oral liquid formulations described herein are prepared from the reconstitution of an enalapril powder formulation. In some embodiments, the enalapril powder formulation comprising enalapril, a sweetener, a preservative, and optionally an excipient is dissolved in water, a buffer, other aqueous solvent, or a liquid to form an enalapril oral liquid formulation. In one embodiment, the sweetening agent is sucralose. In one embodiment, the sweetener is not mannitol. In one embodiment, the sweetening agent is xylitol. In another embodiment, the preservative is sodium benzoate. In one embodiment, the preservative is a paraben preservative. In one aspect, the enalapril powder formulation described herein comprises enalapril, sucralose, and sodium benzoate. In some embodiments, the enalapril powder formulation herein further comprises a flavoring agent. In some embodiments, the enalapril powder formulation herein further comprises one or more buffering agents.

In some embodiments, enalapril or a pharmaceutically acceptable salt thereof, is present in about 0.5% w/w to about 30% w/w of the powder formulation. In other embodiments, enalapril or a pharmaceutically acceptable salt thereof, is present in about 0.5% w/w, about 1% w/w, about 1.5% w/w, about 2% w/w, about 2.5% w/w, about 3% w/w, about 3.5% w/w, about 4% w/w, about 4.5% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, about 10% w/w, about 10.5% w/w, about 11% w/w, about 11.5% w/w, about 12% w/w, about 12.5% w/w, about 13% w/w, about 13.5% w/w, about 14% w/w, about 14.5% w/w, about 15% w/w, about 15.5% w/w, about 16% w/w, about 16.5% w/w, about 17% w/w, about 17.5% w/w, about 18% w/w, about 18.5% w/w, about 19% w/w, about 19.5% w/w, about 20% w/w, about 20.5% w/w, about 21% w/w, about 21.5% w/w, about 22% w/w, about 22.5% w/w, about 23% w/w, about 23.5% w/w, about 24% w/w, about 24.5% w/w, about w/w, about 25.5% w/w, about 26% w/w, about 26.5% w/w, about 27% w/w, about 27.5% w/w, about 28% w/w, about 28.5% w/w, about 29% w/w, about 29.5% w/w, or about 30% w/w of the powder formulation. In some embodiments, enalapril or a pharmaceutically acceptable salt thereof, is present in about 10% w/w to about 25% w/w of the powder formulation. In some embodiments, enalapril maleate is present in about 13.5% w/w of the powder formulation. In some embodiments, enalapril maleate is present in about 19.5% w/w of the powder formulation. In some embodiments, enalapril maleate is present in about 24.5% w/w of the powder formulation. In some embodiments, enalapril is present in about 10.5% w/w of the powder formulation. In some embodiments, enalapril is present in about 14.5% w/w of the powder formulation. In some embodiments, enalapril is present in about 18% w/w of the powder formulation.

In some embodiments, enalapril or a pharmaceutically acceptable salt thereof, is present in about 0.1% w/w to about 1% w/w of the powder formulation. In other embodiments, enalapril or a pharmaceutically acceptable salt thereof, is present in about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, or about 1% w/w of the powder formulation. In some embodiments, enalapril or a pharmaceutically acceptable salt thereof, is present in about 0.4% w/w to about 0.7% w/w of the powder formulation. In some embodiments, enalapril maleate is present in about 0.45% w/w of the powder formulation. In some embodiments, enalapril maleate is present in about 0.6% w/w of the powder formulation. In some embodiments, enalapril is present in about 0.4% w/w of the powder formulation. In some embodiments, enalapril is present in about 0.5% w/w of the powder formulation.

Various amounts and concentrations of other components (sweeteners, buffers, preservatives, and the like) in the enalapril powder formulations are found in the previous section describing the amounts and concentrations for the analogous enalapril oral liquid formulations. For example, in some embodiments where sucralose is present in about 1% w/w to about 30% w/w of the solids in the oral liquid formulation; in an analogous enalapril powder formulation, sucralose would be about 1% w/w to about 30% w/w in the powder formulation. In some embodiments where sodium benzoate is present in about 1% w/w to about 30% w/w of the solids in the oral liquid formulation, in an analogous enalapril powder formulation sodium benzoate is present in about 1% w/w to about 30% w/w in the powder formulation.

Liquid vehicles suitable for the enalapril powder formulations to be reconstituted into an oral solution described herein are selected for a particular oral liquid formulation (solution, suspension, etc.) as well as other qualities such as clarity, toxicity, viscosity, compatibility with excipients, chemical inertness, palatability, odor, color and economy. Exemplary liquid vehicles include water, ethyl alcohol, glycerin, propylene glycol, syrup (sugar or other sweetener based, e.g., Ora-Sweet® SF sugar-free flavored syrup), juices (apple, grape, orange, cranberry, cherry, tomato and the like), other beverages (tea, coffee, soft drinks, milk and the like), oils (olive, soybean, corn, mineral, castor and the like), and combinations or mixtures thereof. Certain liquid vehicles, e.g., oil and water, can be combined together to form emulsions. In some embodiments, water is used for as a vehicle for a enalapril oral liquid formulation. In other embodiments, a syrup is used for as a vehicle for a enalapril oral liquid formulation. In yet other embodiments, a juice is used for as a vehicle for a enalapril oral liquid formulation.

Buffering agents maintain the pH of the liquid enalapril formulation. Non-limiting examples of buffering agents include, but are not limited to sodium bicarbonate, potassium bicarbonate, magnesium hydroxide, magnesium lactate, magnesium gluconate, aluminum hydroxide, aluminum hydroxide/sodium bicarbonate co precipitate, mixture of an amino acid and a buffer, a mixture of aluminum glycinate and a buffer, a mixture of an acid salt of an amino acid and a buffer, and a mixture of an alkali salt of an amino acid and a buffer. Additional buffering agents include citric acid, sodium citrate, sodium tartrate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts. Some buffering agents also impart effervescent qualities when a powder is reconstituted in a solution.

In some embodiments, the reconstituted oral liquid formulation comprises a buffer. In some embodiments, the buffer comprises citric acid and sodium citrate. In further embodiments, the enalapril powder formulation described herein comprises additional excipients including, but not limited to, glidants, flavoring agents, coloring agents and thickeners. Additional excipients such as bulking agents, tonicity agents and chelating agents are within the scope of the embodiments.

Glidants are substances that improve flowability of a powder. Suitable glidants include, but are not limited to, calcium phosphate tribasic, calcium silicate, cellulose (powdered), colloidal silicon dioxide, magnesium silicate, magnesium trisilicate, silicon dioxide, starch, talc and the like. In some embodiments, the enalapril powder formulations described herein comprise a glidant.

In another embodiment, the enalapril powder formulation described herein comprises a flavoring agent or flavorant to enhance the taste or aroma of the formulation in liquid form. Suitable natural or synthetic flavoring agents can be selected from standard reference books, for example Fenaroli's Handbook of Flavor Ingredients, 3rd edition (1995). Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, mixed berry, orange, peach, pear, peppermint, pineapple, raspberry, rose, spearmint, strawberry, tangerine, tea, vanilla, wintergreen, etc. Also useful, particularly where the formulation is intended primarily for pediatric use, is tutti-frutti or bubblegum flavor, a compounded flavoring agent based on fruit flavors. Presently preferred flavoring agents include anise, cinnamon, cacao, orange, peppermint, cherry (in particular wild cherry), grape, bubblegum, vanilla, and mixed berry. Flavoring agents can be used singly or in combinations of two or more.

In further embodiments, the enalapril powder formulation described herein comprises a coloring agent for identity and/or aesthetic purposes. Suitable coloring agents illustratively include FD&C Red No. 3, FD&C Red No. 20, FD&C Red No. 40, FD&C Yellow No. 6, FD&C Blue No. 2, D&C Green No. 5, D&C Orange No. 5, caramel, ferric oxide and mixtures thereof In further embodiments, the enalapril powder formulation described herein comprises a thickener. Thickeners impart viscosity or weight to the resultant liquid forms from the enalapril formulation described herein. Exemplary thickeners include dextrin, cellulose derivatives (carboxymethylcellulose and its salts, ethylcellulose, hydroxyethyl cellulose, methylcellulose, hypromellose, and the like) starches, pectin, polyethylene glycol, polyethylene oxide, trehalose and certain gums (xanthan gum, locust bean gum, etc.).

Additional excipients are contemplated in the enalapril powder formulation embodiments. These additional excipients are selected based on function and compatibility with the the enalapril powder formulation described herein and may be found, for example in Remington: The Science and Practice of Pharmacy, Nineteeth Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999), herein incorporated by reference in their entirety.

In some embodiments, the enalapril oral liquid formulation prepared from the powder formulations described herein are homogenous. Homogenous liquids as used herein refer to those liquids that are uniform in appearance, identity, consistency and drug concentration per volume. Non-homogenous liquids include such liquids that have varied coloring, viscosity and/or aggregation of solid particulates, as well as non-uniform drug concentration in a given unit volume. Homogeneity in liquids are assessed by qualitative identification or appearance tests and/or quantitative HPLC testing or the like. The mixing methods and excipients described herein are selected to impart a homogenous quality to a resultant enalapril oral liquid formulation.

Mixing methods encompass any type of mixing that result in a homogenous enalapril oral liquid formulation. In some embodiments, a quantity of an enalapril powder formulation is added to a liquid vehicle and then mixed by a stirring, shaking, swirling, agitation element or a combination thereof. In certain instances, a fraction of a enalapril powder formulation (i.e., one-half, one-third, one-fourth, etc.) is added to a liquid vehicle, mixed by stirring, shaking, swirling, agitation or a combination thereof, and the subsequent powder fraction(s) is added and mixed. In other embodiments, a liquid vehicle is added to an enalapril powder formulation in a container, for example, a bottle, vial, bag, beaker, syringe, or the like. The container is then mixed by stirring, shaking, swirling, agitation, inversion or a combination thereof. In certain instances, a fractional volume of the liquid vehicle (i.e., one-half, one-third, one-fourth volume, etc.) is added to a enalapril powder formulation in a container, mixed by stirring, shaking, swirling, agitation, inversion or a combination thereof; and the subsequent liquid fraction(s) is added and mixed. In certain instances, a one-half fractional volume of the liquid vehicle is added to an enalapril powder formulation in a container and mixing by shaking; the other one-half fractional volume of the liquid vehicle is then subsequently added and mixed. In any of the above embodiments, mixing (i.e., stirring, shaking, swirling, agitation, inversion or a combination thereof) occurs for a certain time intervals such as about 10 seconds, about 20 seconds, about 30 seconds, about 45 seconds, about 60 seconds, about 90 seconds, about 120 seconds, about 2.5 minutes, about 3 minutes, about 3.5 minutes, about 4 minutes, or about 5 minutes. In embodiments, where there are two or more mixing steps, the time intervals for each mixing can be the same (e.g., 2×10 seconds) or different (e.g., 10 seconds for first mixing and 20 seconds for second mixing) In any of the above embodiments, a enalapril oral liquid formulation is allowed to stand for a period of time such as about 10 minutes, about 20 minutes, about 30 minutes, about 45 minutes, about 1 hour, about 1.5 hours or about 2 hours, to allow any air bubbles resultant from any of the mixing methods to dissipate.

Stability of Enalapril Powder Formulation

The enalapril powder formulations described herein are stable in various storage conditions including refrigerated, ambient and accelerated conditions. Stable as used herein refer to enalapril powder formulations having about 95% or greater of the initial enalapril amount and 5% w/w or less total impurities or related substances at the end of a given storage period. The percentage of impurities is calculated from the amount of impurities relative to the amount of enalapril. Stability is assessed by HPLC or any other known testing method. In some embodiments, the stable enalapril powder formulations have about 5% w/w, about 4% w/w, about 3% w/w, about 2.5% w/w, about 2% w/w, about 1.5% w/w, about 1% w/w, or about 0.5% w/w total impurities or related substances. In other embodiments, the stable enalapril powder formulations have about 5% w/w total impurities or related substances. In yet other embodiments, the stable enalapril powder formulations have about 4% w/w total impurities or related substances. In yet other embodiments, the stable enalapril powder formulations have about 3% w/w total impurities or related substances. In yet other embodiments, the stable enalapril powder formulations have about 2% w/w total impurities or related substances. In yet other embodiments, the stable enalapril powder formulations have about 1% w/w total impurities or related substances.

At refrigerated and ambient conditions, in some embodiments, the enalapril powder formulations described herein are stable for at least 1 week, 2 weeks, 4 weeks, 6 weeks, 8 weeks, 10 weeks, 12 weeks, 16 weeks, 20 weeks, at least 24 weeks, at least 30 weeks, or at least 36 weeks. At accelerated conditions, in some embodiments, the enalapril powder formulations described herein are stable for at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks or at least 12 weeks. Accelerated conditions for the enalapril powder formulations described herein include temperature and/or relative humidity (RH) that are above ambient levels (e.g. 25±4° C.; 55±10% RH). In some instances, an accelerated condition is at about 30° C., about 35° C., about 40° C., about 45° C., about 50° C., about 55° C. or about 60° C. In other instances, an accelerated condition is above 65% RH, about 70% RH, about 75% RH or about 80% RH. In further instances, an accelerated condition is about 40° C. or 60° C. at ambient humidity. In yet further instances, an accelerated condition is about 40° C. at 75±5% RH humidity.

Kits and Articles of Manufacture

For the enalapril powder and liquid formulations described herein, kits and articles of manufacture are also described. Such kits can comprise a carrier, package, or container that is compartmentalized to receive one or more containers such as vials, tubes, and the like, each of the container(s) comprising one of the separate elements to be used in a method described herein including an enalapril powder or liquid formulation. Suitable containers include, for example, bottles, vials, syringes, and test tubes. The containers can be formed from a variety of materials such as glass or plastic.

A kit will typically may comprise one or more additional containers, each with one or more of various materials (such as reagents, optionally in concentrated form, and/or devices) desirable from a commercial and user standpoint for an enalapril powder or liquid formulation described herein. Non-limiting examples of such materials include, but not limited to, buffers, diluents, filters, needles, syringes; carrier, package, container, vial and/or tube labels listing contents and/or instructions for use, and package inserts with instructions for use associated with an enalapril powder or liquid formulation. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

Methods

Provided herein, in one aspect, are methods of treatment comprising administration of the enalapril oral liquid formulations described herein to a subject. In some embodiments, the enalapril oral liquid formulations described herein treat hypertension in a subject. Hypertension as used herein includes both primary (essential) hypertension and secondary hypertension. In certain instances, hypertension is classified in cases when blood pressure values are greater than or equal to 140/90 (systolic/diastolic) mm Hg in a subject. In certain instances, the enalapril oral liquid formulations described herein treat a subject having a blood pressure values are greater than or equal to 140/90 mm Hg. In certain instances, the enalapril oral liquid formulations described herein treat primary (essential) hypertension in a subject. In other instances, the enalapril oral liquid formulations described herein treat secondary hypertension in a subject.

In other embodiments, the enalapril oral liquid formulations described herein treat prehypertension in a subject. Prehypertension as used herein refers to cases where a subject's blood pressure is elevated above normal but not to the level considered to be hypertension. In some instances, prehypertension is classified in cases when blood pressure values are 120-139/80-89 mm Hg. In certain instances, the enalapril oral liquid formulations described herein treat a subject having blood pressure values of 120-139/80-89 mm Hg.

In yet other embodiments, the enalapril oral liquid formulations described herein are prophylactically administered to subjects suspected of having, predisposed to, or at risk of developing hypertension. In some embodiments, the administration of enalapril oral liquid formulations described herein allow for early intervention prior to onset of hypertension. In certain embodiments, upon detection of a biomarker, environmental, genetic factor, or other marker, the enalapril oral liquid formulations described herein are prophylactically administered to subjects.

In further embodiments, the enalapril oral liquid formulations described herein treat heart failure (e.g., symptomatic congestive), asymptomatic left ventricular dysfunction, myocardial infarction, diabetic nephropathy and chronic renal failure. In certain instances, the enalapril oral liquid formulations described herein treat symptomatic congestive heart failure. In other instances, the enalapril oral liquid formulations described herein treat asymptomatic left ventricular dysfunction. In further instances, the enalapril oral liquid formulations described herein treat myocardial infarction. In yet further instances, the enalapril oral liquid formulations described herein treat diabetic nephropathy. In yet further instances, the enalapril oral liquid formulations described herein treat chronic renal failure.

Dosing

In one aspect, the enalapril oral liquid formulations are used for the treatment of diseases and conditions described herein. In addition, a method for treating any of the diseases or conditions described herein in a subject in need of such treatment, involves administration of enalapril oral liquid formulations in therapeutically effective amounts to said subject.

Dosages of enalapril oral liquid formulations described can be determined by any suitable method. Maximum tolerated doses (MTD) and maximum response doses (MRD) for enalapril and/or enalaprilat can be determined via established animal and human experimental protocols as well as in the examples described herein. For example, toxicity and therapeutic efficacy of enalapril and/or enalaprilat can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Enalapril dosages exhibiting high therapeutic indices are of interest. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized. Additional relative dosages, represented as a percent of maximal response or of maximum tolerated dose, are readily obtained via the protocols.

In some embodiments, the amount of a given enalapril oral liquid formulation that corresponds to such an amount varies depending upon factors such as the particular enalapril salt or form, disease condition and its severity, the identity (e.g., weight, sex) of the subject or host in need of treatment, but can nevertheless be determined according to the particular circumstances surrounding the case, including, e.g., the specific agent being administered, the liquid composition type, the condition being treated, and the subject or host being treated.

In some embodiments, the enalapril oral liquid formulations described herein are provided in a dose per day from about 0.01 mg to 100 mg, from about 0.1 mg to about 80 mg, from about 1 to about 60, from about 2 mg to about 40 mg of enalapril. In certain embodiments, the enalapril oral liquid formulations described herein are provided in a daily dose of about 0.01 mg, about 0.05 mg, about 0.1 mg, about 0.2 mg, about 0.4 mg, about 0.6 mg, about 0.8 mg, about 1 mg, about 1.5 mg, about 2 mg, about 2.5 mg, about 3 mg, about 4 mg, about 5 mg, about 6 mg, about 7 mg, about 8 mg, about 9 mg, about 10 mg, about 11 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 76, mg, about 80 mg, about 85 mg, about 90 mg or about 100 mg, or any range derivable therein. In certain instances, the enalapril oral liquid formulations described herein are provided in a dose per day of about 1 mg. In certain instances, the enalapril oral liquid formulations described herein are provided in a dose per day of about 2 mg. In certain instances, the enalapril oral liquid formulations described herein are provided in a dose per day of about 3 mg. In certain instances, the enalapril oral liquid formulations described herein are provided in a dose per day of about 4 mg. In certain instances, the enalapril oral liquid formulations described herein are provided in a dose per day of about 5 mg. In certain instances, the enalapril oral liquid formulations described herein are provided in a dose per day of about 6 mg. In certain instances, the enalapril oral liquid formulations described herein are provided in a dose per day of about 7 mg. In certain instances, the enalapril oral liquid formulations described herein are provided in a dose per day of about 8 mg. In certain instances, the enalapril oral liquid formulations described herein are provided in a dose per day of about 9 mg. In certain instances, the enalapril oral liquid formulations described herein are provided in a dose per day of about 10 mg. In certain instances, the enalapril oral liquid formulations described herein are provided in a dose per day of about 11 mg. In certain instances, the enalapril oral liquid formulations described herein are provided in a dose per day of about 12 mg. The dose per day described herein can be given once per day or multiple times per day in the form of sub-doses given b.i.d., t.i.d., q.i.d., or the like where the number of sub-doses equal the dose per day.

In further embodiments, the daily dosages appropriate for the enalapril oral liquid formulations described herein are from about 0.01 to about 1.0 mg/kg per body weight. In one embodiment, the daily dosages appropriate for the enalapril oral liquid formulations are from about 0.02 to about 0.8 mg/kg enalapril per body weight. In another embodiment, the daily dosage appropriate for the enalapril oral liquid formulations are from about 0.05 to about 0.6 mg/kg per body weight. In another embodiment, the daily dosage appropriate for the enalapril oral liquid formulations is about 0.05 mg/kg, about 0.06 mg/kg, about 0.07 mg/kg, about 0.08 mg/kg, about 0.10 mg/kg, about 0.15 mg/kg, about 0.20 mg/kg, about 0.25 mg/kg, about 0.30 mg/kg, about 0.40 mg/kg, about 0.50 mg/kg, or about 0.60 mg/kg.

In other embodiments the enalapril oral liquid formulations are provided at the maximum tolerated dose (MTD) for enalapril and/or enalaprilat. In other embodiments, the amount of the enalapril oral liquid formulations administered is from about 10% to about 90% of the maximum tolerated dose (MTD), from about 25% to about 75% of the MTD, or about 50% of the MTD. In particular embodiments, the amount of the enalapril oral liquid formulations administered is from about 5%, 10%, 15%, 20%, 25%, 30%, 35%, 40%, 45%, 50%, 55%, 60%, 65%, 70%, 75%, 80%, 85%, 90%, 95%, 99%, or higher, or any range derivable therein, of the MTD for enalapril and/or enalaprilat.

In further embodiments, the enalapril oral liquid formulations are provided in a dosage that is similar, comparable or equivalent to a dosage of a known enalapril tablet formulation. In other embodiments, the enalapril oral liquid formulations are provided in a dosage that provides a similar, comparable or equivalent pharmacokinetic parameters (e.g., AUC, $C_{max}$, $T_{max}$, $C_{min}$, $T_{1/2}$) as a dosage of a known enalapril tablet formulation. Similar, comparable or equivalent pharmacokinetic parameters, in some instances, refer to within 80% to 125%, 80% to 120%, 85% to 125%, 90% to 110%, or increments therein, of the given values. It should be recognized that the ranges can, but need not be symmetrical, e.g., 85% to 105%.

Administration

Administration of an enalapril oral liquid formulation is at a dosage described herein or at other dose levels and formulations determined and contemplated by a medical practitioner. In certain embodiments, the enalapril oral liquid formulations described herein are administered for prophylactic and/or therapeutic treatments. In certain therapeutic applications, the enalapril oral liquid formulations are administered to a patient already suffering from a disease, e.g., hypertension, in an amount sufficient to cure the disease or at least partially arrest or ameliorate the symptoms, e.g., lower blood pressure. Amounts effective for this use depend on the severity of the disease, previous therapy, the patient's health status, weight, and response to the enalapril formulations, and the judgment of the treating physician. Therapeutically effective amounts are optionally determined by methods including, but not limited to, a dose escalation clinical trial.

In prophylactic applications, the enalapril oral liquid formulations described herein are administered to a patient susceptible to or otherwise at risk of a particular disease, e.g., hypertension. Such an amount is defined to be a "prophylactically effective amount or dose." In this use, the precise amounts also depend on the patient's state of health, weight, and the like. When used in a patient, effective amounts for this use will depend on the risk or susceptibility of developing the particular disease, previous therapy, the patient's health status and response to the enalapril formulations, and the judgment of the treating physician.

In certain embodiments wherein the patient's condition does not improve, upon the doctor's discretion the administration of an enalapril oral liquid formulations described herein are administered chronically, that is, for an extended period of time, including throughout the duration of the patient's life in order to ameliorate or otherwise control or limit the symptoms of the patient's disease. In other embodiments, administration of an enalapril oral liquid formulation continues until complete or partial response of a disease.

In certain embodiments wherein a patient's status does improve, the dose of an enalapril oral liquid formulation being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is, by way of example only, by 10%-400%, including by way of example only 10%, 15%, 20%, 25%, 30%, 35%, 40%, 45%, 50%, 55%, 60%, 65%, 70%, 75%, 80%, 85%, 90%, 95%, and 100%.

In some embodiments, enalapril oral liquid formulations described herein are administered chronically. For example, in some embodiments, an enalapril oral liquid formulation is administered as a continuous dose, i.e., administered daily to a subject. In some other embodiments, enalapril oral liquid formulations described herein are administered intermittently (e.g. drug holiday that includes a period of time in which the formulation is not administered or is administered in a reduced amount).

In some embodiments an enalapril oral liquid formulation is administered to a subject who is in a fasted state. A fasted state refers to a subject who has gone without food or fasted for a certain period of time. General fasting periods include at least 4 hours, at least 6 hours, at least 8 hours, at least 10 hours, at least 12 hours, at least 14 hours and at least 16 hours without food. In some embodiments, an enalapril oral liquid formulation is administered orally to a subject who is in a fasted state for at least 8 hours. In other embodiments, an enalapril oral liquid formulation is administered to a subject who is in a fasted state for at least 10 hours. In yet other embodiments, an enalapril oral liquid formulation is administered to a subject who is in a fasted state for at least 12 hours. In other embodiments, an enalapril oral liquid formulation is administered to a subject who has fasted overnight.

In other embodiments an enalapril oral liquid formulation is administered to a subject who is in a fed state. A fed state refers to a subject who has taken food or has had a meal. In certain embodiments, an enalapril oral liquid formulation is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1 hour post-meal, or 2 hours post-meal. In certain instances, an enalapril oral liquid formulation is administered to a subject in a fed state 30 minutes post-meal. In other instances, an enalapril oral liquid formulation is administered to a subject in a fed state 1 hour post-meal. In yet further embodiments, an enalapril oral liquid formulation is administered to a subject with food.

In further embodiments described herein, an enalapril oral liquid formulation is administered at a certain time of day for the entire administration period. For example, an enalapril oral liquid formulation can be administered at a certain time in the morning, in the evening, or prior to bed. In certain instances, an enalapril oral liquid formulation is administered in the morning. In other embodiments, an enalapril oral liquid formulation can be administered at different times of the day for the entire administration period. For example, an enalapril oral liquid formulation can be administered on 8:00 am in the morning for the first day, 12 pm noon for the next day or administration, 4 pm in the afternoon for the third day or administration, and so on.

Further Combinations

The treatment of certain diseases or conditions (e.g., hypertension, heart failure, myocardial infarction and the like) in a subject with an enalapril oral liquid formulation described herein encompass additional therapies and treatment regimens with other agents in some embodiments. Such additional therapies and treatment regimens can include another therapy, e.g., additional anti-hypertensives, for treatment of the particular disease or condition in some embodiments. Alternatively, in other embodiments, additional therapies and treatment regimens include other agents used to treat adjunct conditions associated with the disease or condition or a side effect from the enalapril oral liquid formulation in the therapy.

Additional agents for use in combination with an enalapril oral liquid formulation described herein include, but are not limited to, diuretics (loop, thiazide, potassium-sparing, and the like), beta blockers (metoprolol, propanolol, pronethalol, and the like), alpha blockers (phentolamine, phenoxybenzamine, tamsulosin, prazosin, and the like), mixed alpha and beta blockers (bucindolol, carvedilol, labetalol), calcium channel blockers (dihydropyridines such as nifedipine, amlodipine, etc., dilitazem, verapamil and the like), angiotensin II receptor antagonists (saralasin, lsartan, eprosartin, irbesartan, valsartan, and the like), other ACE inhibitors (captopril, quinapril, ramipril, lisinopril, zofenopril, and the like), aldosterone antagonists (eplerenone, spironolactone and the like), vasodilators (hydralazine and the like) and alpha-2 agonists (clonidine, moxonidine, guanabenz and the like).

Certain Definitions

Unless defined otherwise, all technical and scientific terms used herein have the same meanings as commonly understood by one of ordinary skill in the art. Although any methods and materials similar or equivalent to those described herein can be used in the practice or testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent such as enalapril is directed to the treatment and/or the amelioration of, reversal of, or stabilization of the symptoms of hypertension described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with an enalapril formulation, can include, but is not limited to, providing an enalapril formulation into or onto the target tissue; providing an enalapril formulation systemically to a patient by, e.g., oral administration whereby the therapeutic reaches the target tissue or cells. "Administering" a formulation may be accomplished by injection, topical administration, and oral administration or by other methods alone or in combination with other known techniques.

The term "animal" as used herein includes, but is not limited to, humans and non-human vertebrates such as wild, domestic and farm animals. As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In further instances, the human is 12 years of age or younger. In certain instances, the human is elderly. In other instances, the human is 60 years of age or older. Other examples of subjects include experimental animals such as mice, rats, dogs, cats, goats, sheep, pigs, and cows. The experimental animal can be an animal model for a disorder, e.g., a transgenic mouse with hypertensive pathology. A patient can be a human suffering from hypertension, or its variants or etiological forms.

By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology). As such, a non-limiting example of a "therapeutically effective amount" or "effective amount" of a formulation of the present disclosure may be used to inhibit, block, or reverse the activation, migration, or proliferation of cells or to effectively treat hypertension or ameliorate the symptoms of hypertension.

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease;

amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

EXAMPLES

Example A

Effect of pH on the Formation of Degradants in Enalapril Formulations at 60° C.

Formulations were prepared containing enalapril maleate according to Table A-1. The pH of each solution was recorded. Five milliliters of each formulation were transferred to each of four 3-dram glass screw-capped vials with Teflon inserts in the caps. The vials were placed into a 60° C. heating chamber then one vial removed and analyzed by HPLC at times of zero, ~97 and ~180 hours.

TABLE A-1

Formulation (in mg/mL) of Enalapril Formulations at Varying pH and Citrate Buffer Concentration

| | Formulation (mM citrate) | | | | | |
|---|---|---|---|---|---|---|
| Component | A1 (50) | A2 (50) | A3 (50) | A4 (50) | A5 (50) | A6 (25) |
| Enalapril maleate | 1.0 | 1.0 | 1.0 | 1.0 | 1.0 | 1.0 |
| Mannitol | 50 | 50 | 50 | | 50 | 6.0 |
| Xylitol | | | | 50 | | |
| Citric acid, anhydrous | 7.35 | 5.05 | 2.55 | 5.05 | 5.05 | 2.76 |
| Sodium citrate, dihydrate | 3.45 | 7.0 | 10.8 | 7.0 | 7.0 | 3.15 |
| Sodium benzoate | 1 | 1 | 1 | 1 | 1 | |
| Methylparaben sodium | | | | | 1.75 | 0.335 |
| Propylparaben sodium | | | | | | 0.095 |
| Potassium sorbate | | | | | | 1 |
| Sucralose | 0.75 | 0.75 | 0.75 | 0.75 | 0.75 | 0.75 |
| Silicon dioxide | | | | | | 0.075 |
| Mixed berry flavor (powdered) | 0.5 | 0.5 | 0.5 | 0.5 | 0.5 | 0.5 |
| Water | qs | qs | qs | qs | qs | qs |
| pH | 3.4 | 4.4 | 5.2 | 4.4 | 4.5 | 4.4 | qs = sufficient quantity

The results of the HPLC analysis for the two main degradants in the samples, enalapril diketopiperazine and enalaprilat, are provided in Table A-2.

TABLE A-2

Primary Degradants Present in the Formulations (% w/w of enalapril maleate)

| | Formulation | | | | | |
|---|---|---|---|---|---|---|
| Hours at 60° C. | A1 | A2 | A3 | A4 | A5 | A6 |
| Enalapril Diketopiperazine | | | | | | |
| 0 | 0.04 | 0.03 | 0.03 | 0.03 | 0.03 | 0.03 |
| 97 | 3.10 | 0.88 | 0.33 | 0.86 | 0.70 | 0.53 |
| 180 | 6.21 | 1.77 | 0.75 | 1.73 | 1.43 | 1.07 |

TABLE A-2-continued

Primary Degradants Present in the Formulations (% w/w of enalapril maleate)

| | Formulation | | | | | |
|---|---|---|---|---|---|---|
| Hours at 60° C. | A1 | A2 | A3 | A4 | A5 | A6 |
| Enalaprilat | | | | | | |
| 0 | 0.09 | 0.15 | 0.29 | 0.14 | 0.16 | 0.12 |
| 97 | 5.20 | 16.9 | 47.4 | 16.1 | 20.3 | 15.6 |
| 180 | 9.94 | 34.8 | 113 | 33.5 | 42.2 | 31.7 |

Example B

Effect of Buffer Concentration on the Formation of Degradants in Enalapril Formulations at 60° C.

Formulations were prepared containing enalapril maleate according to Table B-1. The pH of each solution was measured and adjusted as needed to pH 3.3 with ~1N HCl or ~0.5N NaOH. Five milliliters of each formulation were transferred to each of six 3-dram glass screw-capped vials with Teflon inserts in the caps. The vials were placed into a 60° C. heating chamber then two vials were removed and analyzed by HPLC at times of zero, ~66 and ~139 hours.

TABLE B-1

Formulation (in mg/mL) of Enalapril Maleate Formulations at Varying Citrate Buffer Concentrations

| | Formulation | | |
|---|---|---|---|
| Component | B1 (5 mM citrate) | B2 (10 mM citrate) | B3 (20 mM citrate) |
| Enalapril maleate | 1.0 | 1.0 | 1.0 |
| Citric acid, anhydrous | 0.82 | 1.65 | 3.29 |
| Sodium citrate, anhydrous | 0.19 | 0.38 | 0.75 |
| Sodium benzoate | 1.0 | 1.0 | 1.0 |
| Sucralose | 0.7 | 0.7 | 0.7 |
| Mixed berry flavor (powdered) | 0.5 | 0.5 | 0.5 |
| Water | qs | qs | qs |
| pH | 3.3 | 3.3 | 3.3 | qs = sufficient quantity

The results of the HPLC analysis for the two main degradants in the samples, enalapril diketopiperazine and enalaprilat, are provided in Table B-2.

TABLE B-2

Primary Degradants Present in the Formulations
(% w/w of enalapril maleate)

| | Formulation | | |
|---|---|---|---|
| Hours at 60° C. | B1 (5 mM citrate) | B2 (10 mM citrate) | B3 (20 mM citrate) |
| | Enalapril Diketopiperazine | | |
| 0 | 0.01 | 0.01 | 0.01 |
| 66 | 1.57 | 1.63 | 1.79 |
| 139 | 3.70 | 3.94 | 4.24 |
| | Enalaprilat | | |
| 0 | 0.00 | 0.00 | 0.00 |
| 66 | 2.98 | 2.88 | 3.19 |
| 139 | 5.28 | 5.23 | 5.69 |

Example C

Stability of Enalapril Maleate Formulations Containing Paraben Preservatives

Powder formulations were prepared according to Table C-1. All components in each formulation except mannitol or xylitol were added to a 2.5 liter polypropylene screw capped bottle. The bottle was mixed by inversion in a Turbula° mixer for 5 minutes. The mannitol or xylitol was then added and the components mixed for 5 minutes, then the other half of the mannitol or xylitol was added and a final mix of 5 minutes was completed.

One liter of solution formulation was prepared for each formulation by adding an appropriate amount of each powdered formulation to a 1 liter volumetric flask and adding about 500 mL water. The powder was dissolved with mixing then the contents of the flask were brought to 1 liter with additional water. The amount of powder to add was determined such that the final concentration of enalapril maleate was 1.0 mg/mL. Fifty milliliter aliquots of each formulation were placed into HDPE bottles. The bottles were screw-capped and placed into storage at 5° C.±3° C., at room temperature (19-23° C.) and at 40° C.±2° C. At various times, bottles were removed from the storage condition and analyzed.

TABLE C-1

Composition of Enalapril Maleate Formulations

| Component | C1 | C2 | C3 | C4 | C5 |
|---|---|---|---|---|---|
| | Powder Formulation (grams) | | | | |
| Enalapril maleate | 12.3 | 12.3 | 8.86 | 2.16 | 2.16 |
| Mannitol | 74.4 | 74.4 | 394.0 | | |
| Xylitol | | | | 96.6 | 93.7 |
| Citric acid, anhydrous | 28.6 | 35.6 | 28.4 | 5.40 | 5.40 |
| Sodium citrate, anhydrous | 24.5 | 14.7 | 7.73 | 4.10 | 4.10 |
| Sodium methylparaben | 4.17 | 4.17 | 8.86 | 2.16 | 2.16 |
| Sodium propylparaben | 1.10 | 1.10 | | | |
| Potassium sorbate | 12.3 | 12.3 | | | |
| Sodium benzoate | | | 8.86 | 2.16 | 2.16 |
| Xanthan Gum | | | | | 1.62 |
| Colloidal silicon dioxide | 0.859 | 0.859 | 4.43 | | 1.08 |

TABLE C-1-continued

Composition of Enalapril Maleate Formulations

| Component | C1 | C2 | C3 | C4 | C5 |
|---|---|---|---|---|---|
| Sucralose | 9.20 | 9.20 | 6.64 | 1.62 | 1.62 |
| Mixed berry flavor | 6.13 | 6.13 | 4.43 | 1.08 | 1.08 |
| Total solids | 173.5 | 170.7 | 472.3 | 115.2 | 115.2 |
| | Liquid Formulations (mg/mL) | | | | |
| Enalapril maleate | 1.00 | 1.00 | 1.00 | 1.00 | 1.00 |
| Mannitol | 6.07 | 6.07 | 44.5 | | |
| Xylitol | | | | 44.7 | 43.4 |
| Citric acid, anhydrous | 2.33 | 2.90 | 3.21 | 2.50 | 2.50 |
| Sodium citrate, anhydrous | 2.00 | 1.20 | 0.87 | 1.90 | 1.90 |
| Sodium methylparaben | 0.34 | 0.34 | 1.00 | 1.00 | 1.00 |
| Sodium propylparaben | 0.09 | 0.09 | 1.00 | | |
| Potassium sorbate | 1.00 | 1.00 | | | |
| Sodium benzoate | | | 1.00 | 1.00 | 1.00 |
| Xanthan Gum | | | | | 0.75 |
| Colloidal silicon dioxide | 0.07 | 0.07 | 0.50 | | 0.50 |
| Sucralose | 0.75 | 0.75 | 0.75 | 0.75 | 0.75 |
| Mixed berry flavor | 0.50 | 0.50 | 0.50 | 0.50 | 0.50 |
| pH (measured) | 4.4 | 3.8 | 3.7 | 4.4 | 4.6 |

The results of the HPLC analysis for the diketopiperazine and enalaprilat degradants in the samples are provided in Table C-2.

TABLE C-2

Degradant Content After Storage (% w/w of enalapril maleate)

| | Storage | | Formulation | | | | |
|---|---|---|---|---|---|---|---|
| | ° C. | Weeks | C1 | C2 | C3 | C4 | C5 |
| | | | Liquid Formulations | | | | |
| Diketopiperazine | 5 | 0 | 0.03 | 0.04 | 0.04 | 0.02 | 0.02 |
| | | 4 | 0.02 | 0.03 | 0.03 | 0.03 | 0.02 |
| | | 8 | 0.03 | 0.04 | 0.04 | | |
| | 19-23 | 0 | 0.03 | 0.04 | 0.04 | 0.02 | 0.02 |
| | | 4 | 0.05 | 0.09 | 0.11 | 0.05 | 0.04 |
| | | 8 | 0.08 | 0.17 | 0.19 | | |
| | 40 | 0 | 0.03 | 0.04 | 0.04 | 0.02 | 0.02 |
| | | 4 | 0.35 | 0.91 | 1.10 | 0.31 | 0.21 |
| | | 8 | 0.65 | 1.80 | 2.05 | | |
| Enalaprilat | 5 | 0 | 0.18 | 0.14 | 0.12 | 0.13 | 0.19 |
| | | 4 | 0.18 | 0.15 | 0.12 | 0.43 | 0.53 |
| | | 8 | 0.55 | 0.38 | 0.34 | | |
| | 19-23 | 0 | 0.18 | 0.14 | 0.12 | 0.13 | 0.19 |
| | | 4 | 1.35 | 0.83 | 0.80 | 1.75 | 2.29 |
| | | 8 | 3.34 | 2.06 | 1.98 | | |
| | 40 | 0 | 0.18 | 0.14 | 0.12 | 0.13 | 0.19 |
| | | 4 | 10.49 | 6.08 | 6.11 | 12.30 | 16.14 |
| | | 8 | 24.37 | 14.12 | 14.22 | | |

Example D

Stability of Enalapril Maleate Formulations Containing Benzoate Preservative

Powder formulations were prepared according to Table D-1. All components in each formulation except enalapril maleate and mannitol or xylitol were blended with a mortar and pestle. The enalapril maleate was then triturated with the blend. The xylitol or mannitol was then triturated into the blend using a geometric dilution technique.

One liter of solution formulation was prepared for each formulation by adding an appropriate amount of each powdered formulation to a 1 liter volumetric flask and adding about 500 mL water. The powder was dissolved with mixing then the contents of the flask were brought to 1 liter with additional water. The amount of powder to add was determined such that the final concentration of enalapril maleate was 1.0 mg/mL. Fifty milliliter aliquots of each formulation were placed into HDPE bottles. The bottles were screw-capped and placed into storage at 5° C.±3° C., at room temperature (19-23° C.) and at 40° C.±2° C. At various times, bottles were removed from the storage condition and analyzed.

TABLE D-1

Composition of Enalapril Maleate Formulations

| Component | D1 | D2 | D3 | D4 | D5 | D6 |
|---|---|---|---|---|---|---|
| Powder Formulation (grams) | | | | | | |
| Enalapril maleate | 3.63 | 3.63 | 3.63 | 3.63 | 8.86 | 2.16 |
| Xylitol | 537.2 | 176.1 | | 537.2 | | |
| Mannitol | | | 319.4 | | 401.2 | 98.9 |
| Citric acid, anhydrous | 11.9 | 11.9 | 11.9 | 10.4 | 26.6 | 6.48 |
| Sodium citrate, anhydrous | 2.72 | 2.72 | 2.72 | 4.86 | 11.3 | 2.76 |
| Sodium benzoate | 3.63 | 3.63 | 3.63 | 3.63 | 8.86 | 2.16 |
| Rebalance X60 (sucralose and maltodextrin) | | 10.9 | | | | |
| Sucralose | | | | | 6.64 | 1.62 |
| Saccharin sodium | | | | 7.26 | | |
| Colloidal silicon dioxide | | | | | 4.43 | |
| Mixed berry flavor | 1.82 | 1.82 | 1.82 | 1.82 | 4.43 | 1.08 |
| Total solids | 561 | 211 | 350. | 561 | 472.3 | 115.2 |
| Liquid Formulations (mg/mL) | | | | | | |
| Enalapril maleate | 1.00 | 1.00 | 1.00 | 1.00 | 1.00 | 1.00 |
| Xylitol | 148.0 | 48.5 | | 148.0 | | |
| Mannitol | | | 88.0 | | 45.3 | 45.8 |
| Citric acid, anhydrous | 3.29 | 3.29 | 3.29 | 2.85 | 3.00 | 3.00 |
| Sodium citrate, anhydrous | 0.75 | 0.75 | 0.75 | 1.34 | 1.28 | 1.28 |
| Sodium benzoate | 1.00 | 1.00 | 1.00 | 1.00 | 1.00 | 1.00 |
| Rebalance X60 (sucralose and maltodextrin) | | 3.00 | | | | |
| Sucralose | | | | | 0.75 | 0.75 |
| Saccharin sodium | | | | 2.00 | | |
| Colloidal silicon dioxide | | | | | 0.50 | |
| Mixed berry flavor | 0.50 | 0.50 | 0.50 | 0.50 | 0.50 | 0.50 |
| pH (measured) | 3.2 | 3.2 | 3.4 | 3.7 | 3.6 | 3.6 |

The results of the HPLC analysis for the diketopiperazine and enalaprilat degradants in the samples are provided in Table D-2.

TABLE D-2

Degradant Content After Storage (% w/w of enalapril maleate)

| | Storage | | Formulation | | | | | |
| | °C. | Weeks | D1 | D2 | D3 | D4 | D5 | D6 |
|---|---|---|---|---|---|---|---|---|
| | Liquid Formulations | | | | | | | |
| Diketopiperazine | 5 | 0 | 0.04 | 0.02 | 0.03 | 0.03 | 0.04 | 0.04 |
| | | 4 | 0.07 | 0.03 | 0.05 | 0.05 | 0.03 | |
| | | 8 | 0.11 | 0.06 | 0.08 | 0.08 | 0.05 | |
| | | 12 | 0.08 | 0.04 | 0.06 | 0.06 | | |
| | | 26 | 0.11 | 0.07 | 0.09 | 0.07 | | |
| | 19-23 | 0 | 0.04 | 0.02 | 0.03 | 0.03 | 0.04 | 0.04 |
| | | 4 | 0.27 | 0.21 | 0.24 | 0.16 | 0.12 | 0.12 |
| | | 8 | 0.50 | 0.41 | 0.47 | 0.30 | 0.21 | 0.22 |
| | | 12 | 0.62 | 0.52 | 0.58 | 0.35 | | |
| | | 26 | 1.39 | 1.20 | 1.33 | 0.76 | | |
| | 40 | 0 | 0.04 | 0.02 | 0.03 | 0.03 | 0.04 | 0.04 |
| | | 4 | 2.87 | 2.32 | 2.73 | 1.57 | 1.21 | 1.13 |
| | | 8 | 5.13 | 4.42 | 5.44 | 2.97 | 2.23 | 2.16 |
| | | 12 | 6.86 | 5.90 | 6.90 | 3.91 | | |
| | | 26 | 13.63 | 12.18 | 13.56 | 7.74 | | |
| Enalaprilat | 5 | 0 | 0.03 | 0.02 | 0.03 | 0.03 | 0.13 | 0.14 |
| | | 4 | 0.15 | 0.12 | 0.06 | 0.17 | 0.13 | |
| | | 8 | 0.22 | 0.19 | 0.22 | 0.27 | 0.34 | |
| | | 12 | 0.20 | 0.17 | 0.19 | 0.22 | | |
| | | 8 | 0.32 | 0.30 | 0.30 | 0.39 | | |
| | 19-23 | 0 | 0.03 | 0.02 | 0.03 | 0.03 | 0.13 | 0.14 |
| | | 4 | 0.69 | 0.66 | 0.69 | 0.86 | 0.74 | 0.76 |

TABLE D-2-continued

Degradant Content After Storage (% w/w of enalapril maleate)

| Storage | | Formulation | | | | | |
|---|---|---|---|---|---|---|---|
| °C. | Weeks | D1 | D2 | D3 | D4 | D5 | D6 |
| | 8 | 1.38 | 1.33 | 1.41 | 1.68 | 1.83 | 1.82 |
| | 12 | 1.71 | 1.68 | 1.73 | 2.15 | | |
| | 26 | 3.63 | 3.61 | 3.59 | 4.55 | | |
| 40 | 0 | 0.03 | 0.02 | 0.03 | 0.03 | 0.13 | 0.14 |
| | 4 | 4.76 | 4.42 | 4.76 | 6.45 | 5.55 | 5.24 |
| | 8 | 8.95 | 8.64 | 9.61 | 12.94 | 12.73 | 12.18 |
| | 12 | 11.01 | 10.64 | 11.41 | 16.16 | | |
| | 26 | 17.18 | 17.11 | 18.30 | 27.36 | | |

Example E

Stability of Solution Formulations of Enalapril Maleate

Solution formulations were prepared according to Table E-1. Thirty milliliter aliquots of each formulation were placed into HDPE bottles. The bottles were screw-capped and placed into storage at 5° C.±3° C., at room temperature (19-23° C.) and at 40° C.±2° C. At various times, bottles were removed from the storage condition and analyzed.

Composition of Enalapril Maleate Formulations (mg/mL)

| Component | E1 | E2 | E3 | E4 | E5 | E6 |
|---|---|---|---|---|---|---|
| Enalapril maleate | 1.00 | 1.00 | 1.00 | 1.00 | 1.00 | 1.00 |
| Xylitol | 150 | 200 | | 150 | | |
| Citric acid anhydrous | 3.29 | 3.29 | 3.29 | 3.29 | 1.65 | 0.82 |
| Sodium citrate anhydrous | 0.75 | 0.75 | 0.75 | 0.75 | 0.38 | 0.19 |
| Sodium benzoate | 1.00 | 1.00 | 1.00 | 1.00 | 1.00 | 1.00 |
| Sucralose | | | 0.70 | | 0.70 | 0.70 |
| Mixed berry flavor | | | 0.50 | 0.50 | 0.50 | 0.50 |
| Water | qs | qs | qs | qs | qs | qs |
| pH (measured) | 3.3 | 3.3 | 3.3 | 3.4 | 3.3 | 3.3 | qs = sufficient quantity

The results of the HPLC analysis for the diketopiperazine and enalaprilat degradants in the samples are provided in Table E-2.

TABLE E-2

Degradant Content After Storage (% w/w of enalapril maleate)

| | Storage | | Formulation | | | | | |
|---|---|---|---|---|---|---|---|---|
| | °C. | Weeks | E1 | E2 | E3 | E4 | E5 | E6 |
| Diketopiperazine | 5 | 0 | 0.01 | 0.01 | 0.01 | 0.01 | 0.01 | 0.01 |
| | | 4 | 0.04 | 0.04 | 0.05 | 0.04 | 0.03 | 0.03 |
| | | 8 | 0.04 | 0.04 | 0.04 | 0.04 | 0.03 | 0.03 |
| | | 12 | 0.05 | 0.05 | 0.04 | 0.05 | 0.04 | 0.04 |
| | | 26 | 0.07 | 0.06 | 0.05 | 0.06 | 0.05 | 0.05 |
| | | 52 | | | | | 0.15 | 0.14 |
| | | 62 | 0.18 | 0.18 | 0.16 | 0.14 | | |
| | 19-23 | 0 | 0.01 | 0.01 | 0.01 | 0.01 | 0.01 | 0.01 |
| | | 4 | 0.22 | 0.23 | 0.21 | 0.20 | 0.16 | 0.15 |
| | | 8 | 0.35 | 0.35 | 0.32 | 0.31 | 0.29 | 0.28 |
| | | 12 | 0.58 | 0.59 | 0.53 | 0.51 | 0.48 | 0.45 |
| | | 26 | 1.10 | 1.10 | 1.00 | 0.95 | 0.97 | 0.92 |
| | | 52 | | | | | 2.30 | 2.15 |
| | | 62 | 3.02 | 3.04 | 2.75 | 2.64 | | |
| | 40 | 0 | 0.01 | 0.01 | 0.01 | 0.01 | 0.01 | 0.01 |
| | | 4 | 2.65 | 2.71 | 2.60 | 2.42 | 1.76 | 1.68 |
| | | 8 | 4.02 | 3.99 | 3.99 | 3.62 | 3.37 | 3.13 |
| | | 12 | 6.72 | 6.42 | 6.47 | 6.00 | 5.53 | 5.29 |
| Enalaprilat | 5 | 0 | 0.00 | 0.00 | 0.01 | 0.02 | 0.00 | 0.00 |
| | | 4 | 0.07 | 0.09 | 0.10 | 0.11 | 0.07 | 0.08 |
| | | 8 | 0.12 | 0.14 | 0.10 | 0.13 | 0.09 | 0.08 |
| | | 12 | 0.16 | 0.15 | 0.15 | 0.17 | 0.14 | 0.11 |
| | | 26 | 0.31 | 0.30 | 0.29 | 0.31 | 0.27 | 0.24 |
| | | 52 | | | | | 0.54 | 0.46 |
| | | 62 | 0.75 | 0.75 | 0.74 | 0.71 | | |
| | 19-23 | 0 | 0.00 | 0.00 | 0.01 | 0.02 | 0.00 | 0.00 |
| | | 4 | 0.65 | 0.65 | 0.68 | 0.70 | 0.50 | 0.46 |
| | | 8 | 1.17 | 1.19 | 1.20 | 1.23 | 1.03 | 0.95 |
| | | 12 | 1.67 | 1.69 | 1.72 | 1.80 | 1.30 | 1.21 |
| | | 26 | 3.36 | 3.38 | 3.42 | 3.57 | 3.07 | 2.90 |
| | | 52 | | | | | 6.32 | 5.88 |

TABLE E-2-continued

Degradant Content After Storage (% w/w of enalapril maleate)

| Storage | | Formulation | | | | | |
|---|---|---|---|---|---|---|---|
| ° C. | Weeks | E1 | E2 | E3 | E4 | E5 | E6 |
| | 62 | 7.99 | 8.02 | 8.04 | 8.57 | | |
| 40 | 0 | 0.00 | 0.00 | 0.01 | 0.02 | 0.00 | 0.00 |
| | 4 | 4.85 | 4.93 | 5.19 | 5.42 | 3.33 | 3.25 |
| | 8 | 8.08 | 8.06 | 8.56 | 9.01 | 6.65 | 6.35 |
| | 12 | 10.70 | 10.48 | 11.01 | 11.97 | 8.14 | 7.96 |

Example F

Effect of pH on the Formation of Degradants in Enalapril Formulations at 5° C. and 19-23° C.

Figure 2:
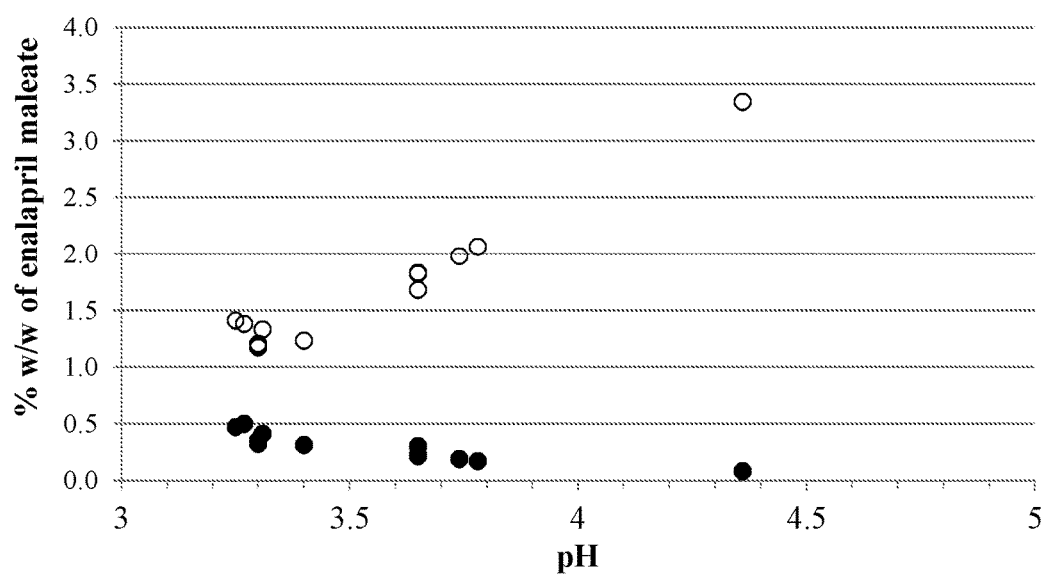
FIG. 2: Effect of pH on degradant formation after 8 weeks of storage of various enalapril solution formulations at room temperature (19-22° C.).

The content of enalapril diketopiperazine and enalaprilat that were formed after 8 weeks of storage for formulations C1-C3 and D1-D5 are plotted in FIG. 1 (5° C.±3° C.) and FIG. 2 (19-23° C. storage). These formulations all contained 20mM total citrate buffer content, but with varying pH. The general effects of formulation pH on the formation of the two main enalapril degradants are shown.

Example G

Antimicrobial Effectiveness Testing of Enalapril Maleate Formulations at pH 3.3

Enalapril formulations were prepared containing differing amounts of the antimicrobial preservative, sodium benzoate. The formulations were then tested for antimicrobial effectiveness (AET) according to the procedures in the 2014 United States Pharmacopeia 37, Chapter <51> for category 3 products. The formulation of the formulations and the AET results are included in Table G-1.

TABLE G-1

Formulation and AET Testing Results

| | Formulation | | | | |
|---|---|---|---|---|---|
| | G1 | G2 | G3 | G4 | G5 |
| Formulation (mg/mL) | | | | | |
| Enalapril maleate | 1.00 | 1.00 | 1.00 | 1.00 | 1.00 |
| Xylitol | 150 | 150 | 150 | 150 | |
| Sucralose | | | | | 0.70 |
| Citric acid, anhydrous | 1.64 | 1.64 | 1.64 | 1.64 | 1.80 |
| Sodium citrate, anhydrous | 0.322 | 0.322 | 0.322 | 0.322 | |
| Sodium citrate, dihydrate | | | | | 0.165 |
| Sodium benzoate | 1.00 | 0.80 | 0.60 | 0.40 | 1.0 |
| Mixed berry flavor | 0.50 | 0.50 | 0.50 | 0.50 | 0.50 |
| Water | q.s. | q.s. | q.s. | q.s. | q.s. |
| HCl/NaOH | | as need to achieve pH | | | |
| Measured pH | 3.3 | 3.3 | 3.3 | 3.3 | 3.3 |
| AET Results | | | | | |
| USP <51> | Pass | Pass | Pass | Pass | Pass | qs = sufficient quantity

Example H

Clinical Trial: Bioavailability Study of 10mg Enalapril Maleate Oral Solution vs. 10mg Epaned® Powder for Oral Solution (Reconstituted) Under Fasted Conditions The objective of this open-label, randomized, two-period, two-treatment, two-way crossover study was to compare the oral bioavailability of a test formulation of 10 mL of enalapril maleate oral solution, 1 mg/mL (formulation E-5), to an equivalent oral dose of the commercially available comparator product, Epaned® (enalapril maleate) Powder for Oral Solution, 1 mg/mL, when administered under fasted conditions in healthy adults.

Study design: Thirty-two healthy adult subjects received a single 10 mL dose of enalapril maleate oral solution, 1 mg/mL, formulation E-5 (Treatment A), in one period and a separate single dose of Epaned Powder for Oral Solution (reconstituted with the supplied Ora-Sweet SF), 1 mg/mL (Treatment B) in another period. Each treatment was administered after an overnight fast of at least 10 hours, followed by a 4-hour fast postdose. Each treatment was administered via a 10 mL oral dosing syringe and followed with 240 mL of room temperature tap water. Each drug administration was separated by a washout period of at least 7 days.

During each study period, meals were the same and scheduled at approximately the same times relative to dose. In addition, during each period, blood samples were obtained prior to and following each dose at selected times through 72 hours postdose. Pharmacokinetic samples were analyzed for enalapril and its metabolite enalaprilat using a validated analytical method; appropriate pharmacokinetic parameters were calculated for each formulation using non-compartmental methods. Blood was also drawn and urine collected for clinical laboratory testing at screening and at the end of the study.

Statistical Methods: The concentration-time data were analyzed using noncompartmental methods in Phoenix™ WinNonlin® (Version 6.3, Pharsight Corporation). Concentration-time data that were below the limit of quantitation (BLQ) were treated as zero in the data summarization and descriptive statistics. In the pharmacokinetic analysis, BLQ concentrations were treated as zero from time-zero up to the time at which the first quantifiable concentration was observed; embedded and/or terminal BLQ concentrations were treated as "missing". Actual sample times were used for all pharmacokinetic and statistical analyses. Analysis of variance (ANOVA) and the Schuirmann's two one-sided t-test procedures at the 5% significance level were applied to the log-transformed pharmacokinetic exposure parameters, $C_{max}$, $AUC_{last}$, and $AUC_{inf}$. The 90% confidence interval for the ratio of the geometric means (Test/Reference) was calculated. Bioequivalence was declared if the lower and upper confidence intervals (CIs) of the log-transformed parameters were within 80% to 125% for enalapril and enalaprilat.

Results: A total of 32 subjects participated in the study and 29 of these subjects completed both study periods. Based on the geometric mean ratios of enalapril and enalaprilat AUCs ($AUC_{last}$ and $AUC_{inf}$), the bioavailability of the enalapril maleate oral solution (formulation E-5) relative to the Epaned Powder for Oral Solution (reconstituted) was approximately 105% to 110%. The geometric mean ratios of enalapril and enalaprilat $C_{max}$ were approximately 115% and 109%, respectively. The 90% CI for comparing the maximum exposure to enalapril and enalaprilat, based on ln ($C_{max}$), was within the accepted 80% to 125% limits. The 90% CIs for comparing total systemic exposure to enalapril and enalaprilat, based on ln ($AUC_{last}$) and ln ($AUC_{inf}$), was within the accepted 80% to 125% limits. Therefore, the test formulation of enalapril maleate oral solution, 1 mg/mL, is bioequivalent to the reference product, Epaned Powder for Oral Solution (reconstituted), 1 mg/mL, under fasted conditions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A stable oral liquid formulation, comprising:
   (i) about 0.6 to about 1.2 mg/ml enalapril or a pharmaceutically acceptable salt or solvate thereof;
   (ii) a buffer comprising about 0.8 to about 3.5 mg/ml citric acid and about 0.1 to about 0.8 mg/ml sodium citrate;
   (iii) about 0.7 to about 1.2 mg/ml sodium benzoate; and
   (iv) water;
       wherein the formulation is stable at about 5±3° C. for at least 12 months; and
       wherein the stable oral liquid formulation has about 95% w/w or greater of the initial enalapril amount and about 5% w/w or less total impurity or related substances at the end of the given storage period.

2. The stable oral liquid formulation of claim 1 further comprising about 0.5 to about 0.9 mg/ml sucralose.

3. The stable oral liquid formulation of claim 1 further comprising a flavoring agent.

4. The stable oral liquid formulation of claim 1, wherein the formulation does not contain mannitol.

5. The stable oral liquid formulation of claim 1, wherein the formulation does not contain silicon dioxide.

6. The stable oral liquid formulation of claim 1, wherein the pH of the stable oral liquid formulation is less than about 3.5.

7. The stable oral liquid formulation of claim 1, wherein the pH of the stable oral liquid formulation is between about 3 and about 3.5.

8. The stable oral liquid formulation of claim 1, wherein the pH of the stable oral liquid formulation is about 3.3.

9. The stable oral liquid formulation of claim 1, wherein the formulation is stable at about 5±3° C. for at least 18 months.

10. The stable oral liquid formulation of claim 1, wherein the formulation is stable at about 5±3° C. for at least 24 months.

11. A stable oral liquid formulation, comprising:
    (i) about 10% to about 25% (w/w of solids) enalapril or a pharmaceutically acceptable salt or solvate thereof;
    (ii) a buffer comprising about 17% to about 47% (w/w of solids) citric acid and about 1% to about 11% (w/w of solids) sodium citrate;
    (iii) about 3% to about 25% (w/w of solids) sodium benzoate; and
    (iv) water;
        wherein the formulation is stable at about 5±3° C. for at least 12 months; and
        wherein the stable oral liquid formulation has about 95% w/w or greater of the initial enalapril amount and about 5% w/w or less total impurity or related substances at the end of the given storage period.

12. The stable oral liquid formulation of claim 11 further comprising about 8% to about 18% (w/w of solids) sucralose.

13. The stable oral liquid formulation of claim 11 further comprising a flavoring agent.

14. The stable oral liquid formulation of claim 11, wherein the formulation does not contain mannitol.

15. The stable oral liquid formulation of claim 11, wherein the formulation does not contain silicon dioxide.

16. The stable oral liquid formulation of claim 11, wherein the pH of the stable oral liquid formulation is less than about 3.5.

17. The stable oral liquid formulation of claim 11, wherein the pH of the stable oral liquid formulation is between about 3 and about 3.5.

18. The stable oral liquid formulation of claim 11, wherein the pH of the stable oral liquid formulation is about 3.3.

19. The stable oral liquid formulation of claim 11, wherein the formulation is stable at about 5±3° C. for at least 18 months.

20. The stable oral liquid formulation of claim 11, wherein the formulation is stable at about 5±3° C. for at least 24 months.

* * * * *